(12) United States Patent
Corbin et al.

(10) Patent No.: US 7,217,527 B2
(45) Date of Patent: May 15, 2007

(54) ASSAY FOR PHOSPHODIESTERASE FUNCTION

(75) Inventors: Jackie D. Corbin, Nashville, TN (US); Sharron H. Francis, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 448 days.

(21) Appl. No.: 10/824,771

(22) Filed: Apr. 15, 2004

(65) Prior Publication Data
US 2004/0266783 A1    Dec. 30, 2004

Related U.S. Application Data

(60) Provisional application No. 60/462,899, filed on Apr. 15, 2003.

(51) Int. Cl.
*G01N 33/53* (2006.01)
*C12Q 1/48* (2006.01)
*C12Q 1/42* (2006.01)

(52) U.S. Cl. ............... 435/7.1; 435/7.2; 435/7.4; 435/7.72; 435/7.9; 435/8; 435/15; 435/19; 435/21; 435/196

(58) Field of Classification Search ............... 435/7.1, 435/7.4, 7.72, 7.9, 8, 21, 7.2, 15, 19, 196
See application file for complete search history.

(56) References Cited

U.S. PATENT DOCUMENTS

| | | | |
|---|---|---|---|
| 6,255,456 B1 * | 7/2001 | Fisher et al. | 530/350 |
| 6,635,437 B2 * | 10/2003 | Akhavan-Tafti et al. | 435/21 |
| 2005/0164298 A1 * | 7/2005 | Golz et al. | 435/7.1 |

OTHER PUBLICATIONS

Ballard et al., "Effects of sildenafil on the relaxation of human corpus cavernosum tissue in vitro and on the activities of cyclic nucleotied phosphodiesterase isozymes," *J. Urol.*, 159:2164-2171, 1998.
Corbin et al., "Phosphorylation of phosphodiesterase-5 by cyclic meucleotide-dependent protein kinase alters its catalytic and allosteric cGMP-binding activities," *Eur. J. Biochem.*, 267:2760-2767, 2000.
Corbin et al., "[3H]sildenafil binding to phosphodiesterase-5 is specific, kinetically heterogeneous, and stimulated by cGMP," *Mol. Pharmacol.*, 63(6):1364-1372, 2003.
Corbin and Francis, "Cyclic GMP phosphodiesterase-5: target of sildenafil," *J. Biol. Chem.*, 274(20):13729-13732, 1999.
Francis et al., "Phosphorylation of isolated human phosphodiesterase-5 regulatory domain induces an apparent conformational change and increases cGMP binding affinity," *J. Biol. Chem.*, 277(49):47581-47587, 2002.
Francis et al., "Single step isolation of sildenafil from commercially available Viagra tablets," *Int. J. Impot. Res.*, 15(5):369-372, 2003.
Gopal et al., "Allosteric sites of phosphodiesterase-5 (PDE5): a potential role in negative feedback regulationo f cGMP signaling in corpus cavernosum," *Eur. J. Biochem.*, 268:3304-3312, 2001.
Okada and Asakawa, "Allosteric activation of cGMP-specific, cGMP-binding phosphodiesterase (PDE5) by cGMP," *Biochemistry*, 41:9672-9679, 2002.
Saenz de Tajada et al., "The phosphodiesterase inhibitory selectivity and the in vitro and in vivo potency of the new PDE5 inhibitor vardenafil," *Int. J. Impot. Res.*, 13(5):282-290, 2001.
Turko et al., "Inhibition of cyclic GMP-binding cyclic GMP-specific phosphodiesterase (type 5) by sildenafil and related compounds," *Mol. Pharmacol.*, 56:124-130, 1999.

* cited by examiner

*Primary Examiner*—Herbert J. Lilling
(74) *Attorney, Agent, or Firm*—Fulbright & Jaworski, LLP

(57) ABSTRACT

The present invention provides filter-based assays for measuring binding of compounds to phosphodiesterases (PDEs). The assay permits stoichiometric binding of compounds to PDEs, thereby providing a highly sensitive measure of a PDE binding and inhibition.

37 Claims, 10 Drawing Sheets

ASSAY FOR PHOSPHODIESTERASE FUNCTION

The present application claims benefit of priority to U.S. Ser. No. 60/462,899, filed Apr. 15, 2003, the entire contents of which are hereby incorporated by reference.

The government owns rights in the present invention pursuant to grant numbers DK 58277 and DK 40029 from the National Institutes of Health.

BACKGROUND OF THE INVENTION

1. Field of the Invention

The present invention relates generally to the fields of enzymology and cell biology. More particularly, it concerns methods for assessing phosphodiesterase function.

2. Description of Related Art

Phosphodiesterase-5 (PDE5), which specifically degrades cGMP, is the target of sildenafil (Pfizer tradename Viagra®) in causing penile erection (Boolell et al., 1996; Corbin & Francis, 1999). PDE5 is present in high levels in smooth muscle tissues, but it is also present in platelets and other tissues (Francis et al., 1990; Francis et al., 2001). PDE5 is believed to contain a single catalytic domain and regulatory domain on each of two subunits. The catalytic domain is highly specific for cGMP, and it is homologous to those of the other family members of the superfamily of cyclic nucleotide phosphodiesterases (PDE) (McAllister-Lucas et al., 1993). The regulatory domain contains two GAF domains (Aravind & Ponting, 1997; McAllister-Lucas et al., 1993; Thomas et al., 1990a) (GAF=cGMP-*Anabaena* adenylate cyclase-*Escherichia coli* FhIA), at least one of which functions as a highly selective allosteric site for cGMP binding (Liu et al., 2001a; McAllister-Lucas et al., 1993). Four other PDE families (PDE2, PDE6, PDE10, and PDE11) also possess GAF domains (Charbonneau, 1990; Charbonneau et al., 1990; Fawcett et al., 2000; Francis et al., 2001; Fujishige et al., 1999; Soderling et al., 1999). In addition to PDE5, two other PDE families (PDE2, PDE6) have been shown to bind cGMP (Stroop & Beavo, 1991; Yamazaki et al., 1980).

Binding of cGMP to the GAF domains of PDE2 stimulates catalytic activity of this enzyme (Beavo et al., 1971). The regulatory domain in PDE5 is phosphorylated by cGMP-dependent protein kinase (PKG) at Ser-92 (bovine) both in vitro and in intact cells (Mullershausen et al., 2001; Murthy, 2001; Rybalkin et al., 2002; Thomas et al., 1990b; Wyatt et al., 1998). Regulation of phosphorylation of this site is substrate-directed since occupation of a GAF domain by cGMP is required for phosphorylation by PKG. Phosphorylation causes stimulation of both catalytic activity and cGMP binding to the GAF domain (Corbin et al., 2000; Francis et al., 2002).

It has been proposed that these effects are responsible for negative feedback regulation of active cGMP levels in cells. For both the cGMP and cAMP signaling pathways, negative feedback regulation has emerged as a major function of PDEs. PDE3 and PDE4 have been reported to be activated by phosphorylation when cAMP is elevated in cells (Conti, 2000; Degerman et al., 1997). Likewise, elevation of cGMP has been shown to cause increased PDE5 activity that is associated with cGMP-sensitive phosphorylation (Mullershausen et al., 2001; Murthy, 2001; Wyatt et al., 1998). In each case, PDE phosphorylation correlates with increased degradation of cyclic nucleotide. Elevation of cGMP is required for phosphorylation of PDE5 by PKG or cAMP-dependent protein kinase (PKA), and this process stimulates degradation of cGMP as well as sequestration of cGMP in the GAF domain (Corbin et al., 2000), both of which represent negative feedback on the cGMP pathway.

Negative feedback regulation of cGMP would be enhanced if cGMP binding to the GAF domain also directly stimulates the catalytic domain. This was predicted earlier from the principle of reciprocity (Thomas et al., 1990a; Weber, 1975; Francis et al., 1990). Binding of 3-isobutyl-1-methylxanthine (IBMX) or a similar ligand to the catalytic domain has been shown to stimulate binding of cGMP to a GAF domain, but direct evidence that binding of cGMP to a GAF domain stimulates the catalytic domain has been elusive. This has been due in large part to difficulties in performing such studies with PDE5, in which both the catalytic domain and GAF domain possess high specificity for cGMP. Okada & Asakawa recently reported that cGMP stimulates PDE5 catalytic activity when measured using a fluorescent cGMP analog that is specific for the catalytic site of the enzyme (Okada & Asakawa, 2002). They suggested that this stimulation occurs through cGMP binding to the GAF domains.

Studies of the catalytic domain of PDE5 would be greatly enhanced by a specific, high-affinity PDE5 catalytic-site radioligand that binds with sufficient affinity to allow isolation of the ligand-enzyme complex. In addition, binding assays based on this interaction could be used to screen for potentially efficacious PDE inhibitors. Properties of the catalytic site that are not directly dependent on catalytic activity could also be examined using such a ligand.

SUMMARY OF THE INVENTION

Thus, there is provided a method of assaying for binding of a test compound to a phosphodiesterase (PDE) comprising (a) providing a PDE; (b) mixing the PDE with a positively-charged peptide or polypeptide and a test compound; (c) passing the mixture of step (b) through a filter; (d) washing the filter with an ionic detergent solution; and (e) measuring test compound associated with the filter, wherein test compound retained on the filter indicates binding of the test compound to the PDE, and wherein the binding of the test compound to PDE is measured at or near stoichiometric levels. The PDE may be PDE1, PDE2, PDE3, PDE5, PDE6, PDE7, PDE8, PDE9, PDE10 or PDE11, or more specifically, PDE2, PDE5, PDE6 or PDE11. The positively-charged peptide or polypeptide may be a histone, such as histone IIA-S, other histones, or poly-L-lysine. The filter may be a paper filter, a nitrocellulose filter, a glass microfiber filter or a quartz microfiber filter, and paper filter may be a Whatman 0.45 μm filter. The method may have step (b) performed at 0° C. to 37° C., and may be at less than 15° C., or at about 4° C. The method may further comprise pre-wetting the filter with an ionic detergent solution, such as Triton X-100. The measuring step may comprise scintillation counting. The PDE may be mixed with the positively-charged polypeptide prior to mixing with the test compound. The PDE may be derived from a tissue extract or be recombinant PDE. The PDE may be purified.

The test compound may be labeled, and measuring may comprise assessing filter-associated label. The may further comprise performing a similar control reaction wherein the mixture lacks PDE, or further comprise performing a similar control reaction wherein the test compound is substituted with a known PDE-binding compound. The known PDE-binding compound may be sildenafil, vardenafil or tadalafil, where the PDE is PDE5. The label may be a radioactive label, a fluorescent label, a dye, a chemiluminescent label, an enzymatic label, or a ligand. The radioactive label may be $^3$H or $^{32}$p. The fluorescent label may be fluorescein, rhodamine, green fluorescent protein, and red fluorescent protein. The chemilluminescent label may be luciferase. Competitive assay formats also are contemplated, where the mixture of step (b) further comprises or is further mixed with a known PDE-binding compound that is labeled (with any of the aforementioned labels), and one will measure filter-associated label, wherein a reduction in filter-associated label, as compared to a similar control reaction lacking the test compound, indicates the test compound binds to the PDE, thereby effectively competing for the labeled PDE binding compound. Again, the known PDE-binding compound is sildenafil, vardenafil or tadalafil, where the PDE is PDE5. The method may further comprise performing a similar control reaction wherein the mixture lacks the test compound. The method may further comprise performing a similar control reaction wherein the mixture lacks the PDE. The binding reaction may contain cGMP or other ligands, and it may utilize phosphorylated PDE in order to stimulate the binding reaction or to quantitate recovery of the PDE.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
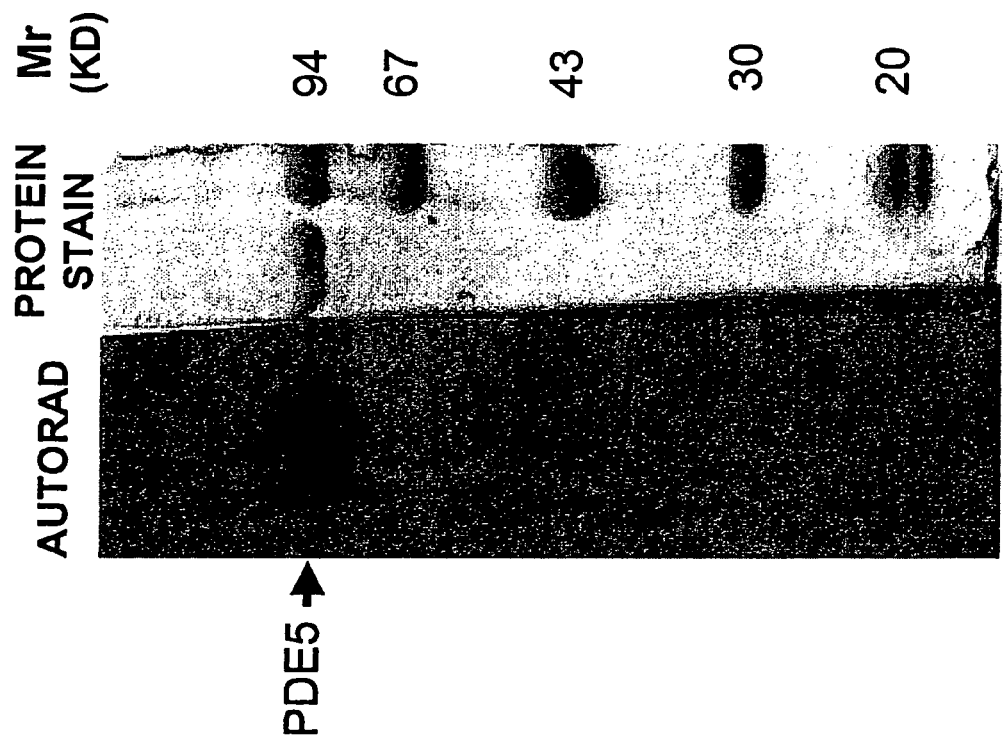
FIG. 1—Purified His-Tag PDE5. Enzyme was expressed and purified as described in Materials and Methods. In order to verify structural and functional integrity, the enzyme was phosphorylated. 200 µl of 4 µM enzyme (final concentration=3.22 µM) was added to 48 µl of a mixture of 10 mM MgCl$_2$-0.1 mM [$^{32}$P]ATP (2000 cpm/pmol), 50 µM cGMP, 0.1 mM IBMX, and 26 µg/ml purified catalytic subunit of PKA for 50 min at 20° C. The mixture was chromatographed on Sephedex G-25 (0.9×13 cm) equilibrated in 10 mM potassium phosphate, pH 6.8, 1 mM EDTA, 25 mM 2-mercaptoethanol (KPM). Fractions (0.5 ml) were collected and 10 µl peak protein fraction (fraction 8) was analyzed for $^{32}$P by scintillation counting, and 10 µl was applied to SDS-PAGE. The gel was stained with Coomassie Brilliant Blue R-250 and developed overnight by autoradiography.

Phosphodiesterases (PDEs) have a wide variety of important biologic functions. As such, finding and improving drugs that modify PDE activity is a very important line of research. An example of the significance of PDEs and inhibitors is illustrated by the drug sildenafil, known as Viagra®, which currently generates hundreds of millions of dollars in sale annually. Clearly, the development of new and improved methods for identifying PDE inhibitors would be of great value to the pharmaceutical industry.

1. The Present Invention

Based on its known competitive inhibition of the catalytic site, its inhibitory potency ($IC_{50}$=1–7 nM at 0.1–0.4 μM cGMP substrate concentrations) and specificity (Ballard et al., 1998; Corbin et al., 2000; Saenz de Tejada et al., 2001), sildenafil was chosen for radiolabeling and use in studies to determine its binding to PDE5. The inventors prepared this compound and other radiolabeled PDE5 inhibitors and successfully employed them as probes for binding studies to explore previously unrecognized features of PDE5. This represents the first report of direct binding of a cGMP analog to the catalytic site of this enzyme.

The present invention thus provides a straightforward assay for measuring the ability of a compound to bind to a PDE. This assay, while simple in design, permits near stoichiometric assessment of binding of putative inhibitors of PDEs. The assay takes advantage of the following features. First, positively-charged peptides or polypeptides, such as histones, are included in the binding reaction. Second, a filter based separation is employed. Third, an ionic detergent is used to wash the filter. The combination of most or all of these elements provides for stoichiometric analysis of PDE binding, which has not previously been achieved.

II. PDE's and PDE Inhibitors

Phosphodiesterases are enzymes that catalyze the degradation of the cyclic nucleotides, cyclic AMP and cyclic GMP, to the corresponding 5' nucleotide monophosphates. Eleven different phosphodiesterases have been described to date. These enzymes exist as homodimers and there is structural similarity between the different families. However, they differ in several respects like selectivity for cyclic nucleotides, sensitivity for inhibitors and activators, physiological roles and tissue distribution. Interest in these enzymes has increased tremendously, both within the medical community and in the general public as a consequence of sildenafil, known as Viagra, the medication recently introduced for the treatment of male erectile dysfunction. Sildenafil mediates its effects by inhibiting phosphodiesterase 5 (PDE5).

To achieve satisfactory erection, normal penile innervation is required. Nitrogen monoxide (nitric oxide), the transmitter substance in these nerves, activates guanylyl cyclase, thereby increasing cyclic GMP production. The increased levels of cyclic GMP cause relaxation of smooth muscles in penile blood vessels and this leads to an erection. Erection is dependent on elevated levels of cyclic GMP and sildenafil mediates its effects by inhibiting the degradation of cyclic GMP by PDE. Other functions that are mediated by PDE5 explain flushing, headaches, heartburn and decreased blood pressure that are some of the side effects seen with sildenafil treatment. Visual disturbances may be explained by slight cross reaction of sildenafil with PDE6.

TABLE 1

| Name | Family | # genes | # splice var. | evid. of add'l splice var. |
| --- | --- | --- | --- | --- |
| PDE1 | CaM-dependent | 3 | 9+ | yes |
| PDE2 | cGMP-stimulated | 1 | 2 | yes |
| PDE3 | cGMP-inhibited | 2 | 2+ | yes |
| PDE4 | cAMP-specific | 4 | 15+ | yes |
| PDE5 | cGMP-specific | 2 | 2 | possible |
| PDE6 | Photoreceptor | 3 | 2 | possible |
| PDE7 | HCP1-PDE | 1 | 1 | possible |
| PDE8 |  | 1 | 1 | possible |
| PDE9 |  | 1 | 4 | possible |
| PDE10 |  | 1 | 2 | possible |
| PDE11 |  | 1 | 4 | possible |

III. Assays and Reagents

A. Producing PDE's

In certain embodiments of the invention, PDE's may be produced from a baculovirus system. Baculovirus vectors are useful tools for the production of proteins for a variety of applications (Summers and Smith, 1987; O'Reilly et al., 1992; also U.S. Pat. No. 4,745,051 (Smith and Summers), U.S. Pat. No. 4,879,236 (Smith and Summers), U.S. Pat. No. 5,077,214 (Guarino and Jarvis), U.S. Pat. No. 5,155,037 (Summers), U.S. Pat. No. 5,162,222, (Guarino and Jarvis), U.S. Pat. No. 5,169,784 (Summers and Oker-Blom) and U.S. Pat. No. 5,278,050 (Summers), each incorporated herein by reference). Baculovirus expression vectors are recombinant insect vectors in which the coding region of a particular gene of interest is placed behind a promoter in place of a non-essential baculoviral gene. The classic approach used to isolate a recombinant baculovirus expression vector is to construct a plasmid in which the foreign gene of interest is positioned downstream of the polyhedrin promoter. Then, via homologous recombination, that plasmid can be used to transfer the new gene into the viral genome in place of the wild-type polyhedrin gene (Summers and Smith, 1987; O'Reilly et al., 1992).

The resulting recombinant virus can infect cultured insect cells and express the foreign gene under the control of the polyhedrin promoter, which is strong and provides very high levels of transcription during the very late phase of infection. The strength of the polyhedrin promoter is an advantage of the use of recombinant baculoviruses as expression vectors because it usually leads to the synthesis of large amounts of the foreign gene product during infection.

*Autographa californica* multinucleocapsid nuclear polyhedrosis virus (AcMNPV) is unusual among baculoviruses because it displays a wider host range than most baculoviruses (Martignoni et al., 1982). AcMNPV is the most extensively studied baculovirus and its genome sequence is known (Ayres et al., 1994). It is distinguished by a unique biphasic life cycle in its lepidopteran host insect (reviewed in Blissard and Rohrmann, 1990). Infection produces high titers of two forms of progeny virus, budded virus (BV) and occlusion derived virus (ODV).

Two routes, adsorptive endocytosis (or viropexis) and direct fusion of BV envelope with plasma membrane, are proposed for entry of BV into cultured cells. Although BV may enter cells by fusion (Volkman et al., 1986), the majority of data indicates that the primary route is by adsorptive endocytosis (Charlton and Volkman, 1993).

In transient systems, the gene of interest is introduced into the cell by infection with a recombinant virus, for example baculovirus. As stated above, in the most widely used baculovirus systems, the gene of interest is under the control of the polyhedrin promoter. The polyhedrin promoter is a very late promoter, which means that the expression of the gene of interest does not start until the late phase of the baculovirus infection. The expression levels are high, but transient as the baculovirus infection eventually leads to cell death.

There are four distinct phases of a baculovirus infection, termed immediate-early, delayed-early, late and very late. Therefore, different baculovirus genes may be classified according to the phase of the viral infection during which they are expressed. Also there are a class of genes which have been defined as early genes, which have not been subcategorized as either immediate-early or delayed-early. Different classes of promoters control each class of gene.

Immediate early promoters are distinguished by needing only host cell factors to drive expression. Examples are the ie1 (Guarino and Summers, 1987), ieN (ie2; Carson et al., 1991) and ie0 promoters. Delayed early promoters are distinguished by needing only products of the immediate-early genes, in addition to host cell factors to drive expression. Examples are the 39K (Guarino and Smith, 1991) and gp64 (Blissard and Rohrmann, 1989; Whitford et al., 1989) promoters. Early promoters have not been placed into the specific immediate-early of delayed-early class. Examples include the DA26, ETL and 35K promoters.

Late promoters requires products of the delayed-early and immediate-early genes, as well as other host cell factors, to drive expression. Examples are the gp64 (Blissard and Rohrmann, 1989; Whitford et al., 1989) and capsid (p39; Thiem and Miller, 1989) promoters. Very late promoters requires a number of baculovirus gene products, in addition to other host cell factors, to drive expression. Examples of promoters from this class are the polyhedrin (Hooft van Iddekinge et al., 1983) and the p10 (Williams et al., 1989) promoters. The best characterized and most often used baculoviral promoter is the polyhedrin promoter. The use of the polyhedrin promoter is a preferred embodiment of the present invention.

Enhancers are DNA elements which can be positionally located to enhance transcription from a given promoter. Enhancers which are active in insect cells to drive transcription are preferred in the present invention. Preferred are viral enhancers, and most preferred are baculoviral enhancers. Examples of baculoviral enhancers include hr1, hr2, hr3, hr4 and hr5 (Guarino et al., 1986).

The term "insect cells" means insect cells from the insect species which are subject to baculovirus infection. For example: *Autographa californica, Bombyx mori, Spodoptera frugiperda, Choristoneura fumiferana, Heliothis virescens, Heliothis zea, Orgyia pseudotsugata, Lymantira dispar, Plutelia xylostella, Malacostoma disstria, Trichoplusia ni, Pieris rapae, Mamestra configurata* and *Hyalophora cecropia*. See U.S. Pat. Nos. 5,498,540 and 5,759,809, incorporated herein by reference. In a particular embodiment, the insect cells are H5 insect cells (Invitrogen, Sorrento, Calif.), derived from *Trichoplusia ni*. Such insect cells may be used in an intact form, or may be used following lyophilization or freeze-thaw cycles.

Insect cells may be cultured according to standard techniques, such as in IPL-41 medium (JRH Biosciences, Inc.) containing 10% fetal calf serum (Hyclone Laboratories, Inc.) as described in U.S. Pat. No. 5,759,809. An alternative procedure for culturing insect cells in media containing fish serum has recently been described. See U.S. Pat. No. 5,498,540, incorporated herein by reference. Cultured insect cells may be transfected with recombinant baculovirus by standard protocols. See, e.g., U.S. Pat. No. 5,759,809, incorporated herein by reference.

B. Purifiying PDE's

In one aspect of the invention, it will be desirable to provide PDEs is a purified form. Purification involves, at one level, the crude fractionation of the cellular milieu to polypeptide and non-polypeptide fractions. Having separated the polypeptide from other proteins, the PDE may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC. Recombinant PDEs can also be expressed by inclusion of a tagged (e.g., His-Tag) amino acid sequence in the enzyme. This facilitates purification on appropriate columns (e.g., nickel) to which the tagged sequence binds.

i. Purification

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur. A "substantially purified" protein or peptide may be essentially free of other proteinaceous materials. A "functionally pure" enzyme may be essentially free of other enzymes.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting more than about 50%, about 60%, about 70%, about 80%, about 90%, about 95%, about 96%, about 97%, about 98%, about 99%, about 99.2%, about 99.4%, about 99.6%, about 99.8%, about 99.9% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

The use of a peptide tag in combination with the methods and compositions of the invention is also contemplated. A tag takes advantage of an interaction between a polypeptide and another substance, such as an a protein, peptide or chemical. A portion of the polypeptide that is involved in the interaction may used as a tag. For instance, the binding region of glutathione-S-transferase (GST) may be used as a tag such that glutathione beads can be used to enrich for a compound containing the GST tag. An epitope tag, which is an amino acid region recognized by an antibody or T cell receptor, may be used. The tag may be encoded by a nucleic acid segment that is operatively linked to a nucleic acid segment encoding CPT I such that a fusion protein is encoded by the nucleic acid molecule. Other suitable fusion proteins are those with β-galactosidase, ubiquitin, hexahistidine (6×His), or the like.

ii. Chromatographic Separation Procedures

Any of a wide variety of chromatographic procedures may be employed according to the present invention. For example, thin layer chromatography, gas chromatography, high performance liquid chromatography, paper chromatography, affinity chromatography or supercritical flow chromatography may be used to effect separation of various chemical species.

Partition chromatography is based on the theory that if two phases are in contact with one another, and if one or both phases constitute a solute, the solute will distribute itself between the two phases. Usually, partition chromatography employs a column, which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a specific-binding-type interaction. The column material is synthesized by covalently coupling one of the binding partners to an insoluble matrix. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The binding partner should be coupled in such a way as to not affect its binding properties. The ligand should also provide relatively tight binding. And it should be possible to elute the substance without destroying the sample or the binding partner. One of the most common forms of affinity chromatography is immunoaffinity chromatography. The generation of antibodies that would be suitable for use in accord with the present invention is discussed below.

iii. Purifications Conditions

As mentioned above, the conditions under which purification is executed may dramatically affect the characteristics of the compounds; for example, the level of activity of PDE may be altered depending upon the conditions employed during any purification scheme. An example of other purification conditions includes the addition of substrates of PDEs, which may stabilize the protein, or other binding partners, such as inhibitors. In addition to temperature conditions, the purification methods may include the use of one or more compounds that are added to a composition containing the molecules to be purified. These additives include detergents, zwitterionic reagents, reducing or oxidizing agents, protease inhibitors, buffers, acids, bases, salts, chelators, preservatives, stabilizers, nucleases, nuclease inhibitors, or any other compound or compounds that affect the activity level of the purified compound. The characteristics could also be altered by PDE5 starting material (e.g., recombinant enzyme, native enzyme, animal species, enzyme truncations or other mutated species).

iv. Detergents

A cell or composition containing PDE may be fractionated in the presence of a detergent or surfactant. The detergent, particularly a mild one that is nondenaturing, can act to solubulize the sample. Detergents may be ionic or nonionic. Examples of nonionic detergents include triton, such as the Triton X series (Triton X-100, Triton X-100R, Triton X-114, Triton X-450, Triton X-450R), octyl glucoside, polyoxyethylene(9)dodecyl ether, digitonin, IGEPAL CA630, n-octyl-beta-D-glucopyranoside (betaOG), n-dodecyl-beta, C12EO7, Tween 20, Tween 80, polidocanol, n-dodecyl beta-D-maltoside (DDM), NP-40, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), and cetyltrimethylammoniumbromide (CTAB). A zwitterionic reagent may also be used in the purification schemes of the present invention, such as Chaps, zwitterion 3–14, and 3-[(3-cholamidopropyl)dimethylammonio]-1-propanesulfonate. It also is contemplated that urea may be added with or without another detergent or surfactant.

v. Reducing Agents and Protease Inhibitors

Other additives that may be used with the purification methods of the present invention include reducing agents and protease inhibitors, which are well known to those of skill in the art. Reducing agents include, for example, 2-mercaptoethanol, dithiothreitol (DTT), pterin, hydrogen sulfide, ascorbic acid, NADPH, and hexamethylphosphorous triamide (Me2N)3P. An example of an oxidizing agent is 5,5'-dithio-bis(2-nitrobenzoic acid) (DTNB). PMSF is an example of a protease inhibitor.

C. Positively-Charged Peptides or Polypeptides

The present invention relies, in one aspect, on the use of positively-charged peptides or polypeptides. Nucleosomes, the primary scaffold of chromatin folding, are dynamic macromolecular structures, influencing chromatin solution conformations (Workman and Kingston, 1998). The nucleosome core is made up of histone proteins, H2A, HB, H3 and H4. Most of the histones are highly positively charged and combine with negatively charged proteins (i.e., PDEs) which would enhance retention of the proteins on filter membranes. Histones also likely bind to the filter membranes themselves, also improving retention. Histone IIA-S (Sigma) has been demonstrated to increase recovery of PDE5 on filter membranes. Optionally, one could use other natural, postively-charged peptides or polypeptides, or synthetic molecules such as poly-L-lysine.

D. Filters

The present invention relies on filters as a substrate for capturing PDE molecules after reaction with putative test compounds. A variety of filters may be employed, including paper filters, nitrocellulose filters, glass microfiber filters and quartz microfiber filters. Of particular utility will be Whatman 0.45 µm filters.

E. Ionic Detergent

In accordance with the present invention, various ionic detergents are utilized in the method to avoid non-specific binding. Of particular value is Triton-X100. The following is an extensive list of other ionic detergents.

i. Anionic Detergents

For use according to the present invention, the following anionic detergents may be employed: Chenodeoxycholic acid, minimum 98%, Chenodeoxycholic acid sodium salt, minimum 97%, Cholic acid, ox or sheep bile, minimum 98%, Dehydrocholic acid, Deoxycholic acid, minimum 99%, Deoxycholic acid, SigmaUltra, minimum 99%, Deoxycholic acid methyl ester, approx. 98%, Digitonin, Solid, Digitonin, cholesterol determination, approx. 50% (TLC), Digitoxigenin, N,N-Dimethyldodecylamine N-oxide, Docusate sodium salt, minimum 99%, Waxy solid, Docusate sodium salt, SigmaUltra, minimum 99%, Glycochenodeoxycholic acid sodium salt, minimum 97% (TLC), Glycocholic acid hydrate, synthetic, minimum 97% (TLC), Glycocholic acid sodium salt hydrate, synthetic, minimum 97% (TLC), Glycodeoxycholic acid monohydrate, minimum 97% (TLC), Glycodeoxycholic acid sodium salt, minimum 97%, Glycodeoxycholic acid sodium salt, SigmaUltra, minimum 97% (TLC), Glycolithocholic acid 3-sulfate disodium salt, Glycolithocholic acid ethyl ester, N-Lauroylsarcosine sodium salt, minimum 94%, N-Lauroylsarcosine sodium salt, SigmaUltra, minimum 97%, N-Lauroylsarcosine solution, minimum 95%, N-Lauroylsarcosine solution, 20%, Lithium dodecyl sulfate, for electrophoresis, denatured polyacrylamide gel electrophoresis, especially at lower temperature conditions, approx. 99% (GC), Lithium dodecyl sulfate, minimum 98.5% (GC), Lithium dodecyl sulfate, SigmaUltra, >99% (GC), Lugol solution, Niaproof 4, Type 4, approx. 27%, Niaproof 4, SigmaUltra, Type 4, approx. 27%, 1-Octanesulfonic acid sodium salt, SigmaUltra, 1-Octanesulfonic acid sodium salt, approx. 98%, Sodium 1-butanesulfonate, Sodium 1-decanesulfonate, SigmaUltra, approx. 98%, Sodium 1-decanesulfonate, approx. 98%, Sodium 1-dodecanesulfonate, Sodium 1-heptanesulfonate anhydrous, Solid, Sodium 1-heptanesulfonate anhydrous, SigmaUltra, Sodium 1-nonanesulfonate, approx. 98%, Sodium 1-propanesulfonate monohydrate, Sodium 2-bromoethanesulfonate, minimum 98%, Sodium cholate hydrate, ox or sheep bile, minimum 99%, Sodium cholate hydrate, SigmaUltra, minimum 99%, Sodium choleate, Sodium deoxycholate, minimum 97%, Sodium deoxycholate monohydrate, SigmaUltra, >99% (titration), Sodium dodecyl sulfate, minimum 98.5% (GC), Sodium dodecyl sulfate, approx. 95% as based on total alkyl sulfate content, Sodium dodecyl sulfate, SigmaUltra, >99% (GC), Sodium hexanesulfonate anhydrous, approx. 98%, Sodium hexanesulfonate anhydrous, SigmaUltra, Sodium octyl sulfate, approx. 95%, Sodium pentanesulfonate anhydrous, Sodium pentanesulfonate anhydrous, SigmaUltra, Sodium taurocholate, ox bile, Sodium taurocholate, minimum 97% (TLC), Taurochenodeoxycholic acid sodium salt, Taurodeoxycholic acid sodium salt monohydrate, SigmaUltra, minimum 97% (TLC), Taurodeoxycholic acid sodium salt monohydrate, minimum 97% (TLC), Taurohyodeoxycholic acid sodium salt hydrate, minimum 98%, Taurolithocholic acid 3-sulfate disodium salt, Tauroursodeoxycholic acid sodium salt, approx. 90%, Trizma® dodecyl sulfate, TWEEN® 80, SigmaUltra, and Ursodeoxycholic acid, minimum 99%.

ii. Cationic

For use according to the present invention, the following cationic detergents may be employed: Alkyltrimethylammonium bromide, Benzalkonium chloride, Semisolid, Benzalkonium chloride, SigmaUltra, Benzyldimethylhexadecylammonium chloride, Benzyldimethyltetradecylammonium chloride, Benzyldodecyldimethylammonium bromide, Benzyltrimethylammonium tetrachloroiodate, minimum 98% (titration), Dimethyldioctadecylammonium bromide, Dodecylethyldimethylammonium bromide, Dodecyltrimethylammonium bromide, SigmaUltra, approx. 99%, Dodecyltrimethylammonium bromide, approx. 99%, Ethylhexadecyldimethylammonium bromide, Girard's reagent T, Crystalline, Hexadecyltrimethylammonium bromide, minimum 99%, Powder, Hexadecyltrimethylammonium bromide, SigmaUltra, approx. 99%, N,N',N',-Polyoxyethylene(10)-N-tallow-1,3-diaminopropane, Liquid, Thonzonium bromide, and Trimethyl(tetradecyl)ammonium bromide, approx. 99%.

iii. Zwitterionic

For use according to the present invention, the following zwitterionic detergents may be employed: CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio) propanesulfonate inner salt, 3-(Dodecyldimethylammonio) propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio)propanesulfonate inner salt, and 3-(N,N-Dimethylpalmitylammonio)propanesulfonate.

F. Labels and Detection

In one aspect of the invention, applicants will provide a PDE, PDE inhibitors or a candidate substance that has been labeled with a detectable label. Detectable labels include, but are not limited to, a radioactive label, a fluorescent label, a dye, a chemilluminescent label, an enzymatic label, or a affinity ligand. Labeled PDE inhibitors are particularly useful in competitive assay formats, where binding of a candidate to PDE may be assessed by the loss of signal, i.e., the loss of PDE inhibitor binding to PDE, in the presence of an unlabeled candidate. Detection of labels may be performed by standard methodologies including scintillation counting and radiography (radioactive label), microscopy and automated plate readers (fluorescent, chemilluminescent, dye), and columns or affinity assays (ligand).

G. Candidate Substances

As used herein, the term "candidate substance" refers to any molecule that may potentially modulate PDE function. The candidate substance may be a protein or fragment thereof, or an organopharmaceutical. The term "candidate modulator" may be used in place of "candidate substance." It may prove to be the case that the most useful pharmacological compounds will be compounds that are structurally related to compounds which interact naturally with a PDE. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a PDE, and then design a molecule for its ability to interact with the PDE. Alternatively, one could design a partially functional fragment of a PDE (binding, but no activity), thereby creating a competitive inhibitor. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be a peptide, a polypeptide, small molecule or any other compound that may be designed through rational drug design starting from known inhibitors of hypertrophic response.

It will, of course, be understood that the screening methods of the present invention are useful in themselves notwithstanding the fact that effective candidates may not be found. The invention provides methods for screening for such candidates, not solely methods of finding them. Further, in an extension of any of the previously described screening assays, the present invention also provide for methods of producing the candidate substance. Thus, methods may further comprise an additional step of "producing the candidate substance identified."

IV. Therapies

A. Disease States

The present invention provides for identification of PDE inhibitors that may be used in treating various diseases and disorders. For example, PDE3 is associated with cardiovascular disease, diabetes and obesity. PDE4 is associated with asthma, inflammation and depression. PDE5 is associated with erectile dysfunction, female sexual dysfunction, pulmonary hypertension, Raynaud's phenomenon, and heartburn. PDE6 is associated with retinitis pigmentosa.

B. Drug Formulations and Routes for Administration to Patients

Pharmaceutical compositions comprising PDE inhibitors will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived. from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Materials. [$\gamma$-$^{32}$P]ATP was from PerkinElmer (NEN)(Boston, Mass.). [$^3$H]cGMP, Sephadex G-25 and DEAE-Sephacel were from Amersham Pharmacia Biotech (Piscataway, N.J.). IBMX, histone IIA-S, *Crotalus atrox* snake venom, 5'-GMP and cGMP were purchased from Sigma Chemical Company (St. Louis, Mo.). Bovine heart catalytic subunit of PKA (Flockhart & Corbin, 1984) and regulatory domain of PDE5 (Liu et al., 2001a) were purified to homogeneity as described earlier. Native bovine lung PDE5 was purified through the Blue Sepharose chromatography step as described (Francis and Corbin, 1988; Thomas et al., 1990a). After obtaining approval from the Committee for the Protection of Human Subjects at Vanderbilt University Medical Center, two-gram segments of lung were obtained from patients undergoing lung transplantation. Segments were excised under sterile conditions from the explanted lung and immediately frozen in liquid nitrogen. The PDE5-specific inhibitor T-0156 was a gift from Tanabe Seiyaku Co. Ltd. (Saitama, Japan).

Sildenafil and radiolabeled sildenafil. Two 50-mg tablets of Viagra™ (Pfizer tradename) were placed into 100 ml H$_2$O in a plastic beaker and broken into fine particles with a glass rod. The suspension and 20 ml rinse were placed into a 200-ml graduated cylinder with plastic covering and shaken manually for 15 min. Residual material was removed by centrifugation for 20 min at 27,000 g at 4° C. Supernatant (120 ml) was applied to a 285 ml Sephadex G-25 (superfine) column equilibrated in deionized H$_2$O at 20° C. Nucleotides, PDE inhibitors, and other compounds with similar structures are known to adsorb to Sephadex G-25, and this resin has been used successfully to purify these compounds (Corbin et al., 1988). After washing the G-25 column with 1.5 liters of H$_2$O, sildenafil was eluted with 500 ml 1% formic acid. The sample was lyophilized, resuspended in H$_2$O, and re-lyophilized. The fluffy crystals were carefully collected from the lyophilization flask and used for experiments and for preparation of radiolabeled sildenafil. Recovery was >80%. Molar extinction coefficient (289 nm) of 13.8 ($\epsilon \times 10^3$) at pH 5.2 was determined using a sample of sildenafil kindly provided by Pfizer. Sample was either stored in crystalline form or in solution of 0.1% formic acid. Molecular weight of sildenafil (474 g/mol) was confirmed by positive ion nanospray and MALDI mass spectrometry, and no significant levels of impurities were detected. 6.7 mg sildenafil purified as described above was sent to Amersham Pharmacia Biotech (Piscataway, N.J.) for tritium labeling. Stock solution was 6 Ci/mmol and 34 µM. Tritium label is expected on the methyl and propyl groups of the pyrazole ring.

Figure 10:
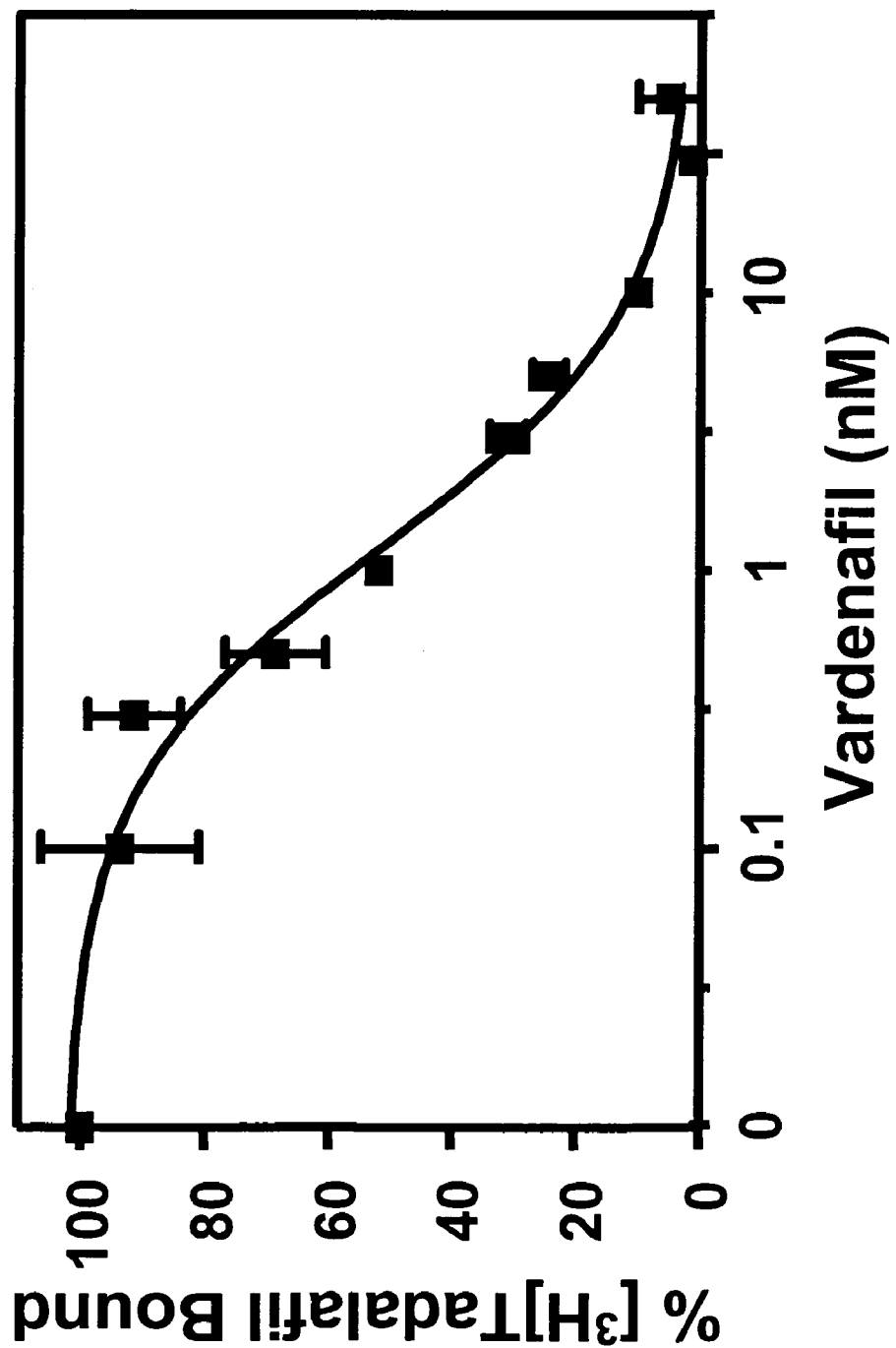
FIG. 10—Determination of $EC_{50}$ for vardenafil. Increasing concentrations of unlabeled vardenafil were included in 2 ml of binding reaction mixture that contained 3 nM [$^3$H]tadalafil. PDE5 was then added (80 μl; 0.035 nM final concentration in assay). Data represent three experiments (n=3), each of which was performed in triplicate.

For the studies shown in FIG. 10, tadalafil was synthesized according to U.S. Pat. No. 6,140,329. After confirming the compound structure by mass spectrometry, tadalafil was submitted to Amersham Biosciences Inc. for radiolabeling with tritium. Sildenafil was purified from tablets of Viagra™ following the method previously established in this laboratory (Corbin et al., 2003). Purified sildenafil was submitted to Amersham Biosciences Inc. for radiolabeling with tritium. HPLC results from Amersham indicated that [$^3$H]sildenafil was >98% pure while the [$^3$H]tadalafil preparation was >99% pure. [$^3$H]vardenafil was provided by Bayer HealthCare A.G., Wuppertal, Germany. All [$^3$H]inhibitors that had been stored for over a year were subjected to Sephadex G-25 chromatography, which adsorbs PDE inhibitors and provides high resolution (Corbin et al., 2003; Francis et al., 2003). All three [$^3$H]inhibitors were resolved in single peaks and co-eluted with purified unlabeled inhibitors, suggesting that the [$^3$H]inhibitors were unaltered after storage.

His-Tag PDE5. The full-length bovine PDE5 cDNA in BacPAK9 (Clontech) purified by QIAGEN was starting material (Turko et al., 1996). The product was amplified using PCR to introduce Sfo I on both the 5' and 3' end and subcloned into pFASTBAC HTc expression vector from GIBCO/Invitrogen. The vector has a rTEV protease site so that the tag and linker region can be cleaved off. DNA was confirmed by sequencing before transformation and transfection into Sf9 cells.

Transformation of PDE5 construct into DH10Bac (Invitrogen) for transposition into the bacmid. 1.5 µg DNA was added to 100 µl DH10BAC cells, and the mixture was incubated on ice for 30 minutes. The mixture was heat-shocked in 42° C. water bath for 45 seconds then chilled on ice for 2 minutes. 900 µl SOC medium was added, and the mixture was placed in a 37° C. shaking incubator with medium agitation for 4 hours. 1:20 dilution of this mixture was made using SOC medium, and 100 µl was plated on Luria Agar plates containing (50 µg/ml kanamycin, 7 µg/ml gentamicin, 10 µg/ml tetracycline, 100 µg/ml Bluo-gal (GIBCO/BRL), 40 µg/ml IPTG). After a 24-hour incubation, 2 white colonies were selected to set up a liquid culture consisting of 2 ml LB medium supplemented with 50 µg/ml kanamycin, 7 µg/ml gentamicin and 10 µg/ml tetracycline. The cultures were grown at 37° C. shaking at 250 rpm for 36 hours. The bacmid DNA was prepared using procedures in GIBCO/BRL Instruction Manual for Bac-to-Bac (TM) Baculovirus Expression system (Invitrogen). Presence of high molecular weight bacmid DNA was confirmed using agarose gel electrophoresis.

Transfection of Sf9 cells with PDE5 recombinant bacmid DNA. The following is a modified transfection procedure recommended by GIBCO/Invitrogen. The Sf9 cells used for transfection were grown in Grace's Insect Media (TM GIBCO/BRL) supplemented with 10% FBS as well as L-glutamine. 0.9 million cells were seeded per well of a 6-well plate and allowed to attach for at least 1 hour. Meanwhile, two solutions were prepared in 14 ml conical tubes. The first solution contained 5 µl of bacmid DNA diluted in 100 µl of Grace's Insect medium without any FBS or L-glutamine. 6 µl of CELLFECTIN reagent (GIBCO/Invitrogen) was diluted in 100 µl Grace's Insect Medium in the second solution. The solutions were combined, mixed, and incubated for 30 minutes at room temperature. The cells were washed twice with 2 ml Grace's Insect Medium. 800 µl Grace's Insect medium was added to the tube containing the CELLFECTIN and PDE5 bacmid DNA. The wash media was aspirated, and the transfection mixture was added to the cells. The cells were incubated for 5 hours at 27° C. The 1-ml mixture was removed from the well, and 2 ml fresh Grace's Insect Medium containing 10% FBS and L-glutamine was added to the well. The cells were incubated for 72 hours at 27° C. The virus was harvested after 72 hours and amplified. Small scale expression tests of the amplified virus were performed by infecting cells in a 6-well plate with varying amounts of virus.

Expression and purification of His-Tag PDE5. Two ml virus was added to 2.5 L Sf9 cells ($1.3 \times 10^6$ cells) that were incubated in a spinner flask for 5 days at 37° C. in a tissue culture incubator. Cells were centrifuged at 2000 rpm in a Beckman JA-10 rotor for 10 min at 4° C. Pellet was broken up with a pipet using 10 ml lysis buffer (20 mM Tris, pH 8, containing 100 mM NaCl) and homogenized twice for 4 sec using Ultraturrax. After centrifugation at 9000 rpm in a Beckman JA-20 rotor for 20 min, supernatant was collected and loaded on a 0.9×3 cm Ni-NTA Agarose (Qiagen) column equilibrated with lysis buffer. The column was washed with 20 ml of lysis buffer before eluting with 30 ml lysis buffer containing 0.1 M imidazole. Fractions (2 ml) were collected and analyzed for cGMP PDE catalytic activity, protein (Bradford, 1976), and SDS-PAGE. Peak fractions of PDE activity were pooled, diluted 5-fold with $H_2O$, and loaded on DEAE-Sephacel (0.9×4 cm) equilibrated in 10 mM potassium phosphate (pH 6.8) and 15 mM β-mercaptoethanol (KPM). After washing with 20 ml KPM containing 50 mM NaCl, PDE5 was eluted with 60 ml of a linear NaCl gradient (50–300 mM) in KPM. Two-ml fractions were collected and analyzed for cGMP PDE catalytic activity, protein, and SDS-PAGE. Peak fractions were pooled, glycerol was added to a final concentration of 20% and aliquots were quick-frozen in liquid nitrogen and stored at −70° C. His-Tag PDE5 was highly pure as indicated by protein staining after SDS-PAGE (FIG. 1). The enzyme had a specific enzyme activity of 7 µmol/min/mg which compared favorably with our previously published value for native bovine PDE5 (5 µmol/min/mg) (Thomas et al., 1990a). His-Tag PDE5 was phosphorylated by catalytic subunit of PKA to a stoichiometry of 0.2 mol per subunit in 50 min at 20° C. (Thomas et al., 1990b). Enzyme phosphorylation and catalytic properties verified structural and functional integrity of this PDE5 preparation.

PDE and PKG assays. PDE activity was determined by a modified assay (Martins et al., 1982) as described earlier (Gopal et al., 2001) using 0.4 µM [$^3$H]cGMP as substrate. PKG activity was determined in the presence of 2 µM cGMP as described (Gopal et al., 2001).

[$^3$]sildenafil membrane filtration binding assays. Method A: 80 µl His-tagged PDE5 (final concentration in reaction=0.77 nM) was added to 2 ml 10 mM KPM containing 0.2 mg/ml histone IIA-S. Various concentrations of [$^3$H] sildenafil were added to the KPM-histone mixture before starting the reaction with enzyme. This order of addition prevented [$^3$H]sildenafil binding to the tube surface, which occurred when [$^3$H]sildenafil was added in absence of histone, and 0.2 mg/ml histone produced the optimum effect. It was also determined that histone had a marked effect to increase retention of PDE5 on the membranes. Reactions were incubated on an ice water bath for 20 min. 200 µl 25%

Triton X-100 (2.2% final concentration) was added to each and samples were rapidly filtered under house vacuum through Millipore nitrocellulose membranes (0.45μ) that had been pre-wetted with 1.5 ml of cold 10 mM potassium phosphate, pH 6.8 (KP), containing 0.1% Triton X-100. Inclusion of Triton X-100 lowered blank values significantly. Tubes were each rinsed with 3 ml of the same buffer and filtered. The filter membranes were removed and placed into slots of a scintillation vial box for subsequent drying. The vial box was placed into a glassware dryer for 10 min, and dried papers were transferred to 6 ml scintillation vials. Five ml non-aqueous scintillant was added, and papers were counted in a scintillation counter. Using purified [$^{32}$P]PDE5 prepared by phosphorylation in presence of cGMP, Mg[$^{32}$P] ATP and catalytic subunit of PKA followed by Sephadex G-25 chromatography (FIG. 1 legend) (Corbin et al., 2000), recovery of PDE5 by Millipore filters was determined to be 75%. Accordingly, [$^3$H]sildenafil binding values were corrected for 25% loss of PDE5 through the filter.

Method B: Reactions were carried out exactly as described in Method A (no Triton X-100 was added to the samples at the end of incubation). Samples were rapidly filtered under house vacuum using a Brandel Cell Harvester with Whatman GF/B glass fiber filters that had been pre-wetted with 1.5 ml cold KP containing 0.1% Triton X-100. After immobilization, filters were washed with 6 ml cold KP buffer containing 0.1% Triton X-100. After washing, filters were removed for drying and counting as described for Method A. Using the same technique employed for calculating recovery of PDE5 in Method A, recovery was 97% using Method B, and the blank was at least 2 times lower using Method B. Maximum [$^3$H]sildenafil binding stoichiometry was 0.31 and 0.61 mol/PDE5 subunit using Method A and B, respectively. This suggested that some bound [$^3$H]sildenafil was lost during filtration, particularly with Method A.

Example 2

Results

Figure 2:
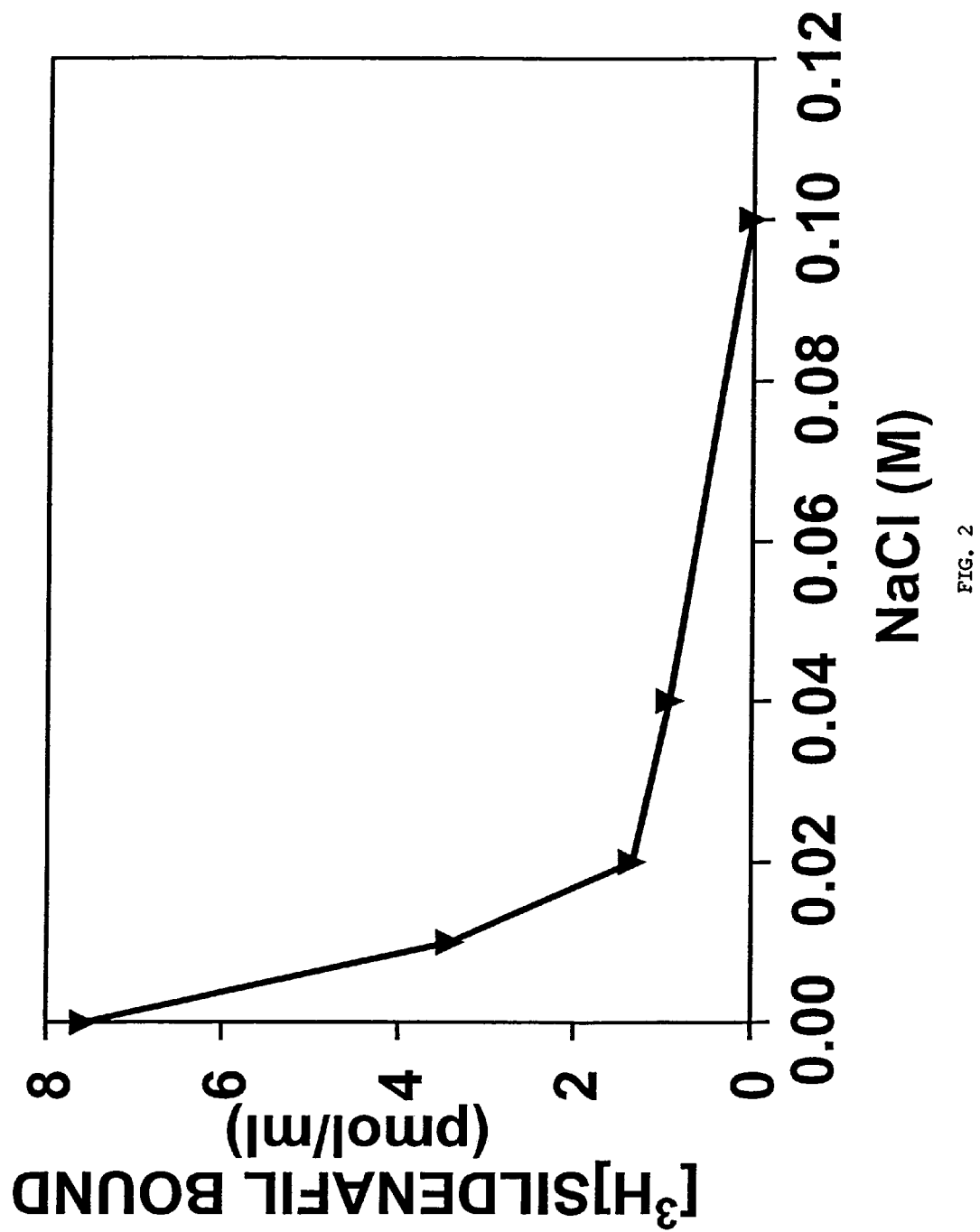
FIG. 2—Effect of NaCl on the [$^3$H]sildenafil-binding assay. Reactions were performed with His-Tag PDE5 using Method A as described in Materials and Methods except that the indicated concentration of NaCl was added to the reaction. PDE5 concentration added was 20 pmol/ml (final assay concentration=0.77 pmol/ml) and final [$^3$H]sildenafil concentration was 12 pmol/ml. Binding units are pmol/ml of added PDE5.

[$^3$H]sildenafil-binding assay. Highly purified His-Tag PDE5 was used for most of the experiments (FIG. 1). [$^3$H]sildenafil binding to PDE5 reached equilibration within 1 min of incubation at all concentrations tested, and using 30 nM [$^3$H]sildenafil, binding was linear with increasing concentrations of PDE5 up to 23 nM (not shown). Binding of [$^3$H]sildenafil to PDE5 using Method A required the presence of low ionic strength conditions (FIG. 2). Increasing ionic strength had less effect using Method B, where 50 mM NaCl inhibited binding by only 40% (not shown). In absence of NaCl, the buffer (potassium phosphate) used for the assay was also inhibitory at concentrations greater than 10 mM. At 30 mM potassium phosphate [$^3$H]sildenafil binding was inhibited by 90% (not shown) compared to binding obtained with 10 mM potassium phosphate, which yielded the same values as 5 mM potassium phosphate.

Figure 3:
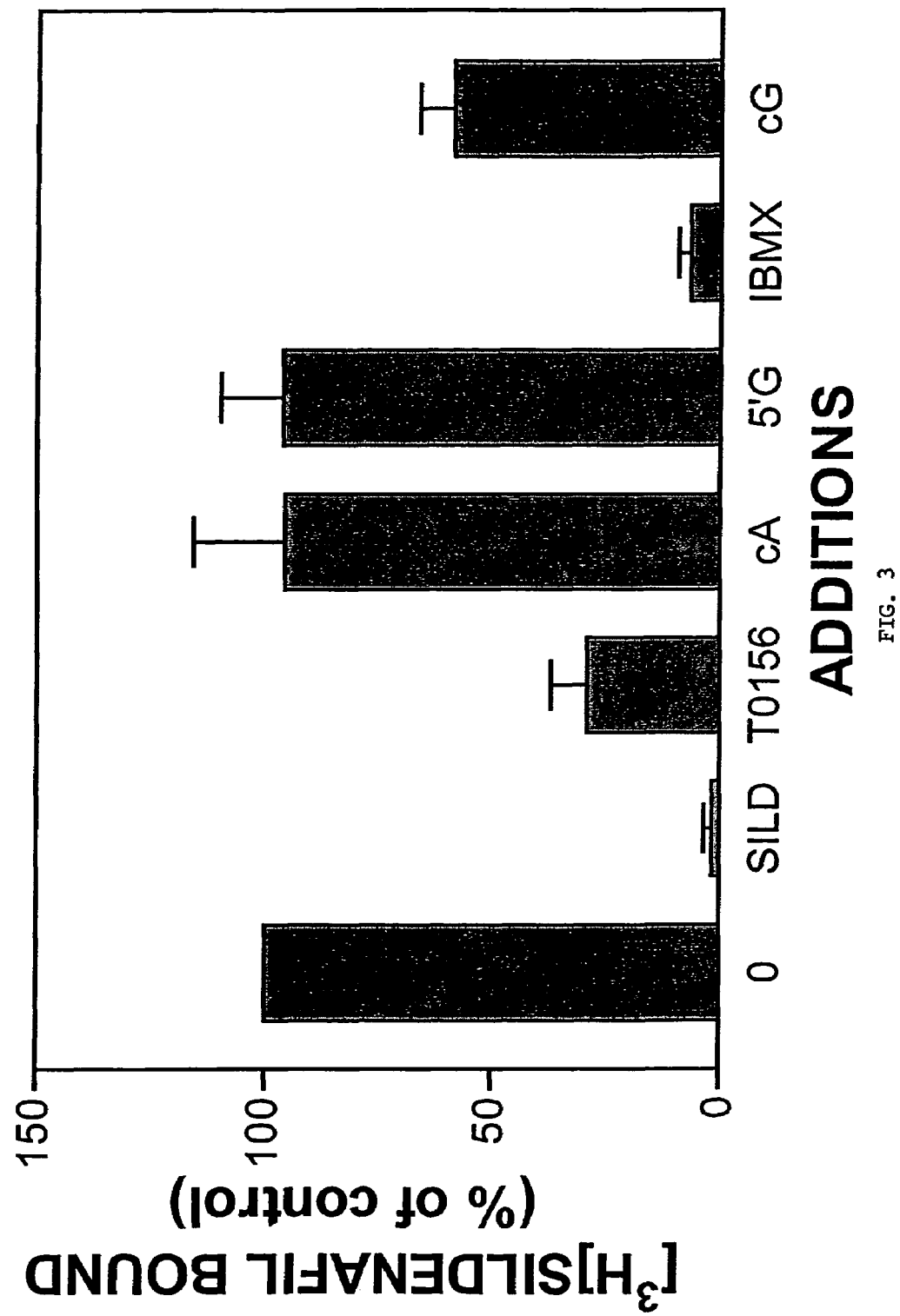
FIG. 3—Effects of nucleotides and unlabeled sildenafil on [$^3$H]sildenafil binding to PDE5. Reactions were performed with His-Tag PDE5 using Method A as described in Materials and Methods. PDE5 concentration added was 20 pmol/ml (final assay concentration=0.77 pmol/ml) and final [$^3$H] sildenafil concentration was 6 pmol/ml. Binding units are pmol/ml added PDE5. Concentrations of competing compounds: unlabeled sildenafil (SILD)=0.083 µM (n=9), T-0156 (PDE5 inhibitor from Tanabe)=0.083 µM (n=6), cAMP (cA)=1.4 mM (n=9), 5'-GMP (5'G)=1.4 mM (n=9), IBMX=0.36 mM (n=6), cGMP (cG)=1.4 mM (n=6).

Specificity for [$^3$H]sildenafil binding to PDE5. Specificity for [$^3$H]sildenafil binding was examined by testing the effects of various compounds on 6 nM [$^3$H]sildenafil binding to purified PDE5 (FIG. 3). Fourteen-fold excess of unlabeled sildenafil or the PDE5-specific inhibitor T-0156 (Tanabe Seiyaku) were strongly inhibitory for [$^3$H]sildenafil binding while 233,000-fold excess of either cAMP or 5'-GMP had no significant effect. The non-specific PDE inhibitor IBMX (0.36 mM) inhibited binding by more than 90%. 233,000-fold excess of cGMP was partially inhibitory, which may be explained by the relatively low affinity of cGMP for the catalytic site coupled with a balance between competition of cGMP with [$^3$H]sildenafil at the catalytic site and stimulation of [$^3$H]sildenafil binding by cGMP binding at the allosteric GAF domain (vide infra). Other unlabeled PDE inhibitors added at 14-fold excess, including vinpocetine (PDE1 inhibitor), EHNA (PDE2 inhibitor), cilostamide (PDE3 inhibitor), or rolipram (PDE4 inhibitor), had no significant effect (not shown). Combined data indicated that [$^3$H]sildenafil binds specifically to the catalytic site of PDE5.

The inventors reported earlier that sildenafil does not interact significantly with the GAF domains of PDE5 (Turko et al., 1999). This conclusion was based on the finding that sildenafil, even at high concentrations, does not compete with [$^3$H]cGMP for binding to the GAF domains of PDE5. Further proof for lack of sildenafil binding to the GAF domains is our results from studies of [$^3$H]sildenafil binding to the highly purified isolated regulatory domain of PDE5. This regulatory domain binds cGMP specifically and with high affinity (Liu et al., 2001a). However, at concentrations of this domain of 0.38–38 nM, and using Method A, 12 nM [$^3$H]sildenafil did not detectably bind to this domain (not shown). This experiment included a positive control of [$^3$H]sildenafil binding to intact PDE5 (0.77 nM) performed as described in FIG. 3.

Figure 4:
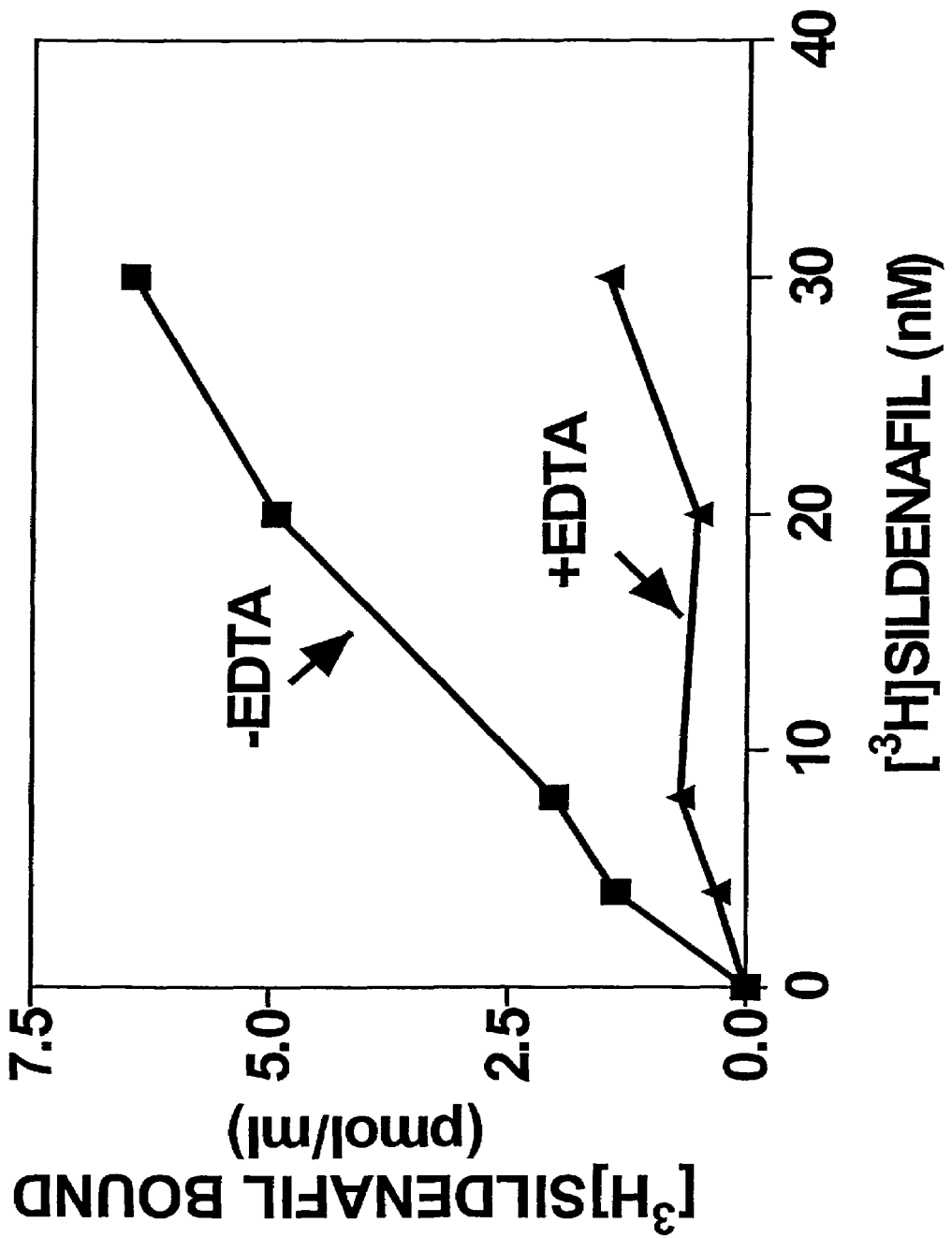
FIG. 4—Effect of EDTA on [$^3$H]sildenafil binding to PDE5. Experiment was performed +/−10 mM EDTA using His-Tag PDE5 in a similar manner as in FIG. 3, except that the [$^3$H]sildenafil concentration was varied between 4 and 30 pmol/ml.

The inventors have demonstrated that PDE5 binds $Zn^{++}$ and that catalytic activity of this enzyme requires $Zn^{++}$ or other divalent cation (Francis et al., 1994). In FIG. 4 it can be seen that 10 mM EDTA strongly inhibits binding of 0.5–30 nM [$^3$H]sildenafil, suggesting that divalent metal is not only necessary for PDE5 catalysis but is also required for structural integrity of the catalytic site. Since PDE5 catalytic activity is known to require divalent cation, these results also further supported catalytic-site specificity of [$^3$H]sildenafil binding to PDE5.

Figure 5:
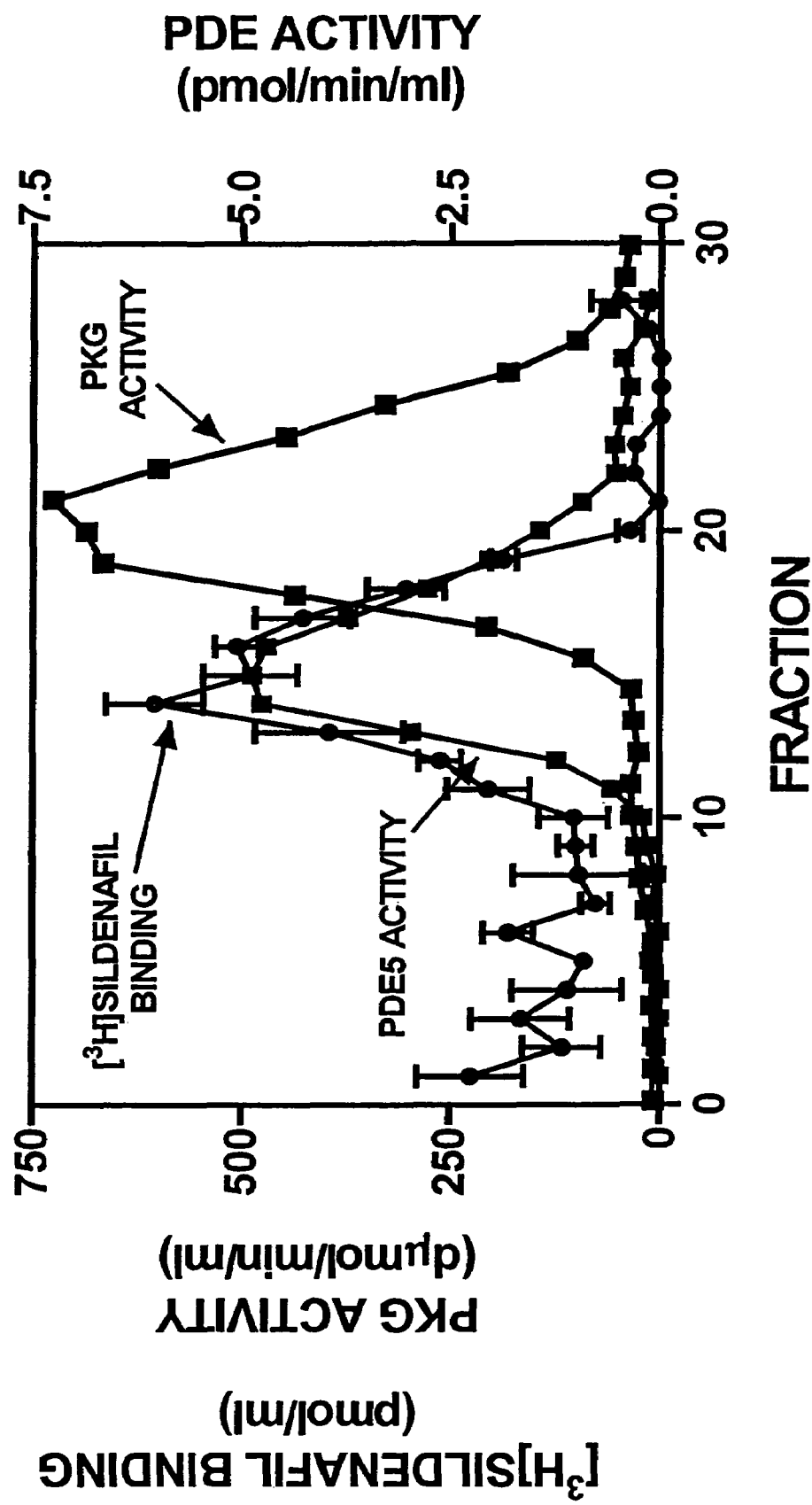
FIG. 5—DEAE-Sephacel chromatography of crude human lung extract. 5 g human lung was thawed, cut into small pieces and homogenized in 80 ml 2.5 mM potassium phosphate (pH 6.8) containing 0.25 mM EDTA, 0.025 mM IBMX, 4 mM β-mercaptoethanol, and 1 mM CaCl$_2$ with a Cuisinart apparatus (high speed) using 3 bursts of 15 sec each at 4° C. After centrifugation in a Beckman JA-20 rotor for 30 min at 10,000×g, 72 ml supernatant was applied to a DEAE-Sephacel column (0.9×10 cm) equilibrated in KPM and the column was washed with 20 ml of KPM containing 20 mM NaCl and 1 mM CaCl$_2$. The column was developed with a linear (20–280 mM) NaCl gradient in KPM containing 1 mM CaCl$_2$. Fractions (1.8 ml) were collected and analyzed (substrate=0.4 µM [$^3$H]cGMP) for PDE activity −/+40 pmol/ml sildenafil in order to calculate PDE5-specific PDE activity. A second peak of cGMP PDE activity eluted just after PDE5 and this activity, which was not inhibited by sildenafil, accounted for about 35% of the total cGMP PDE activity in the profile. [$^3$H]sildenafil binding activity was measured using 400 µl aliquots using Method A as described in Materials and Methods except [$^3$H]sildenafil final concentration was 16 nM. PKG activity was determined in the presence of 2 µM cGMP as described in Materials and Methods.

[$^3$H]Sildenafill binding in crude extract of human lung. Lung tissue is known to be a rich source of PDE5 (Francis et al., 2001). In order to seek additional proof for specificity of [$^3$H]sildenafil binding to PDE5, a supernatant fraction of human lung homogenate was prepared. Fractions were analyzed for PDE5-specific PDE activity and for [$^3$H]sildenafil-binding activity. It can be seen in FIG. 5 that these two activities co-eluted, and no other significant peak of [$^3$H]sildenafil-binding activity was detected. The high resolution of proteins by this procedure was indicated by the elution position of endogenous PKGIα, which was used as marker in the experiment. The NaCl concentration at which the PDE5 peak eluted was only 0.04 M lower than that at which the PKG peak eluted. Only trace binding activity was detected in the flow-through/wash fraction and in a 20 ml of 800 mM NaCl wash fraction collected following termination of the linear NaCl gradient. When the amount of PDE5 in the peak fraction was calculated using the specific enzyme activity of PDE5 at 0.4 μM cGMP as substrate (0.4 μmol/min/mg) a value of 12 nM was obtained. This was approximately double that obtained by direct [$^3$H]sildenafil binding activity (5–6 nM) from the left ordinate. This would be expected since maximum binding stoichiometry of [$^3$H]sildenafil using Method A for purified PDE5 was 0.35 mol/mol, suggesting loss of some bound [$^3$H]sildenafil during filtration. Therefore, quantification of PDE5 by PDE activity and [$^3$H]sildenafil binding activity yielded very similar values, suggesting absence or very low levels of inhibitors or activators of the binding assay after DEAE chromatography. Estimation of PDE5 content in rabbit corpus cavernosum using both PDE activity and cGMP-binding activity yielded similar values to each other (Gopal et al., 2001). The combined results suggested that [$^3$H]sildenafil binding activity can be used as a new method to identify and quantify PDE5 in crude systems. The results also imply that in human lung tissue, which has a high content of smooth muscle, sildenafil has strong selectivity for PDE5 over any other protein including other PDEs.

Figure 6:
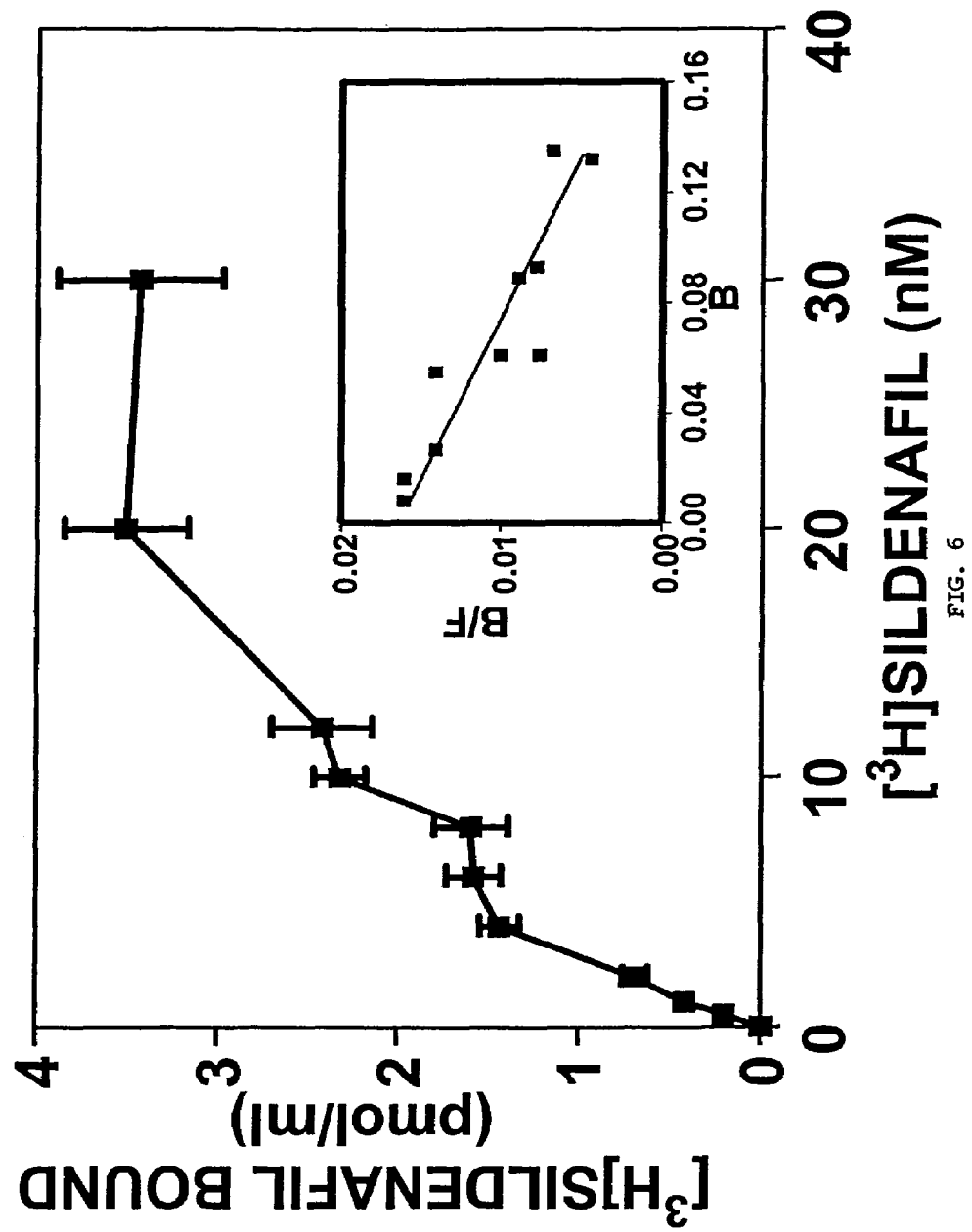
FIG. 6—Effect of [$^3$H]sildenafil concentration on binding to PDE5. Conditions were as described in FIG. 3 using Method A. PDE5 concentration added was 20 pmol/ml (final assay concentration=0.77 pmol/ml), and [$^3$H]sildenafil concentration was varied between 0.5 and 30 pmol/ml. Binding units are pmol/ml added PDE5. Values are mean+/−SEM for 18 determinations. Prism graphics (non-linear regression) were used to calculate K$_D$. Scatchard plot of the data is shown in the inset.

[$^3$H]Sildenafil binding affinity. Dependence of [$^3$H] sildenafil concentration on binding to PDE5 in absence of cGMP using His-Tag PDE5 is shown in FIG. 6. Using non-linear regression analysis with Prism graphics, the $K_D$ was calculated to be 13.3±3.0 nM (n=18). Scatchard plot of the same data (FIG. 6, inset) revealed $K_D$=11.7±1.8 nM. The Goodness of Fit ($R^2$) for non-linear regression of the isotherm shown in FIG. 6 and linear regression of the Scatchard plot was only 0.83 and 0.84, respectively. Therefore, the presence of more than one component of [$^3$H]sildenafil binding could not be ruled out. The $K_D$ value obtained using binding assay Methods A and B (vide infra) in absence of cGMP was similar. Similar results were also obtained using either the peak fraction of crude human bovine lung PDE5 of FIG. 5 or partially purified native bovine PDE5 (not shown).

Figure 7:
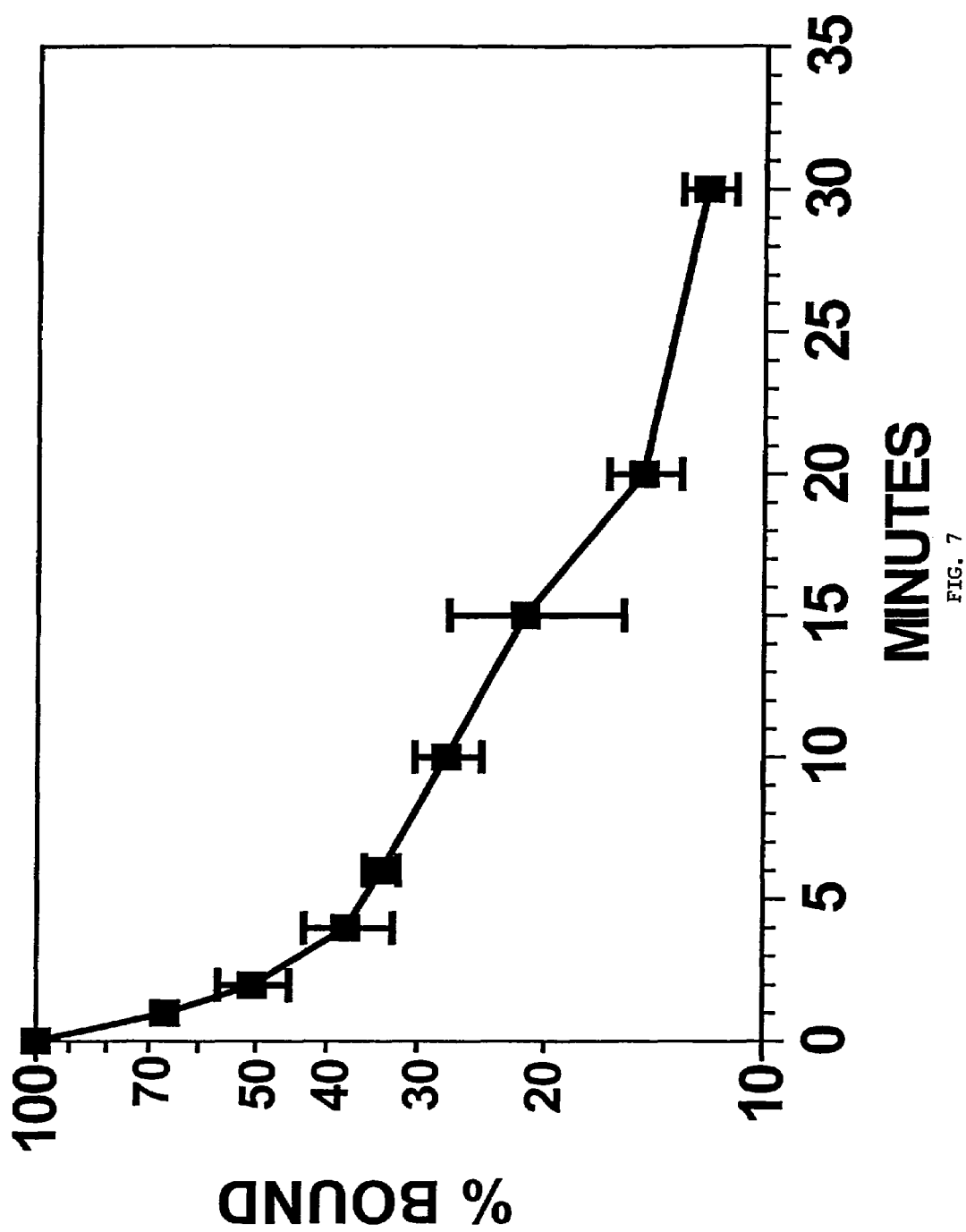
FIG. 7—[$^3$H]sildenafil exchange dissociation from PDE5. 950 µl His-Tag PDE5 (~1 nM final concentration) was added to 4500 µl KPM-0.2 mg/ml histone IIA-S containing 30 pmol/ml [$^3$H]sildenafil for 10 min at 0° C. For the zero-time sample, 550 µl aliquot was added to 200 µl 25% Triton X-100 and filtered as described in Method A. Five µl of 0.6 µmol/ml unlabeled sildenafil was then added to the remaining reaction mixture. 550 µl aliquots were removed at the times indicated and pipetted into 200 µl 25% Triton X-100 and filtered as described in Method A.

Dissociation behavior of PDE5-bound [$^3$H]sildenafil was examined in absence of cGMP and in presence of excess unlabeled sildenafil (FIG. 7). PDE5 was first saturated with 30 nM [$^3$H]sildenafil using the conditions described in FIG. 6. Then exchange of [$^3$H]sildenafil was initiated by addition of 117-fold excess of unlabeled sildenafil. The time course of exchange indicated the presence of two components with $t_{1/2}$ of 14 min and 1.0 min, respectively. The slow component extrapolated back to the Y-axis at approximately the 50% mark, indicating that the two components were present in approximately equal amounts. Assuming diffusion-limited association of [$^3$H]sildenafil to PDE5, and using the equation $K_D$=6.93×10$^{-7}$ M·sec/$t_{1/2}$, $K_{D1}$ was 0.83 nM and $K_{D2}$ was 12 nM. The average of these two $K_D$ values was calculated to be 3.1 nM, which was similar to the $K_D$ value of 4.8 nM determined using direct binding of [$^3$H]sildenafil in presence of cGMP in FIG. 9. The finding of two components of [$^3$H]sildenafil binding using [$^3$H]sildenafil dissociation behavior suggested caution in interpreting the results of FIG. 6, in which a single [$^3$H]sildenafil binding component in PDE5 was assumed for calculation of the binding properties.

Determining of $EC_{50}$. The affinity for binding of PDE5 inhibitors can also be measured by assessing their potencies to compete with labeled [$^3$H]sildenafil or other labeled PDE5 inhibitors. The value obtained by this approach is termed $EC_{50}$. This value should approach the $IC_{50}$ and $K_D$ values. The advantage of the $EC_{50}$ approach is that only one radiolabeled PDE5 inhibitor is required to screen many unlabeled PDE5 inhibitors.

Figure 8:
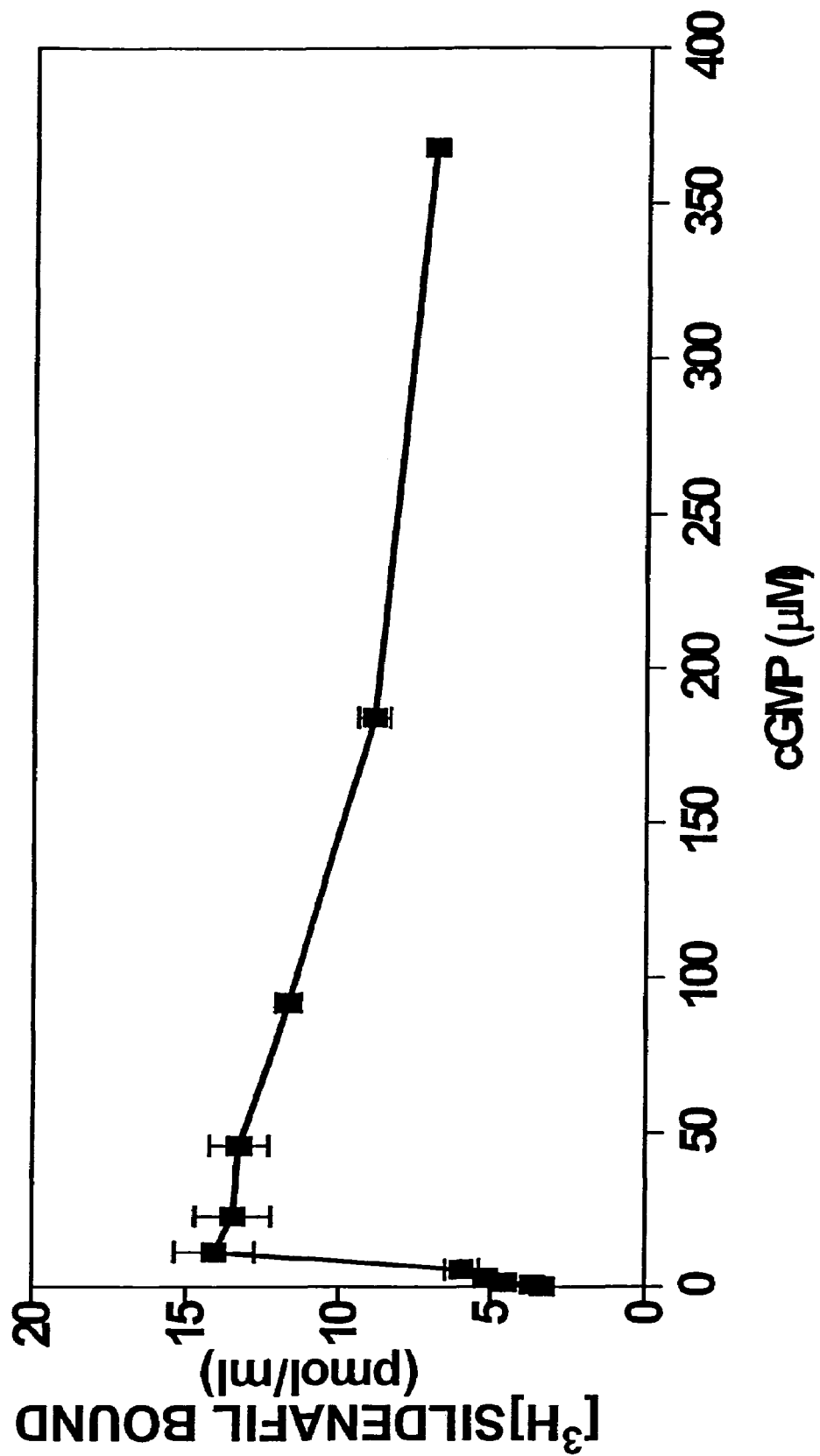
FIG. 8—Effect of cGMP concentration on [$^3$H]sildenafil binding to PDE5. Conditions were as described in Materials and Methods except cGMP was varied between 0 and 368 nmol/ml and [$^3$H]sildenafil was 5 pmol/ml. His-Tag PDE5 final concentration was 1.5 pmol/ml (added concentration=40 pmol/ml). Units are pmol/ml added PDE5. Values are mean±SEM of triplicates in a single experiment. The experiment was performed three times with similar results. Filtration was performed as described for Method B.

Effect of cGMP on [$^3$H]sildenafil binding. The high selectivity of sildenafil for the catalytic site over the GAF domains of PDE5 (Turko et al., 1999) permitted studies of effects of cGMP binding to the GAF domains on the catalytic site. Using Method B with 5 nM [$^3$H]sildenafil in the binding reaction, the inventors have examined the effect of cGMP concentration on [$^3$H]sildenafil binding to PDE5 (FIG. 8). Experiments were done in absence of MgATP and protein kinases so that effects of phosphorylation could be avoided. Low concentrations of cGMP (<10 μM) caused progressive increases in [$^3$H]sildenafil binding, and the stimulatory effect waned at concentrations higher than 10 μM cGMP. Concentrations higher than 1 mM cGMP were inhibitory for [$^3$H]sildenafil binding (FIG. 3). It is suggested that low concentrations of cGMP bind to the allosteric GAF domains and cause direct stimulation of [$^3$H]sildenafil binding to the PDE5 catalytic site. Higher concentrations of cGMP bind both to the GAF domains as well as to the catalytic site. This latter effect causes progressive decrease in [$^3$H]sildenafil binding at >10 μM cGMP. At very high cGMP, only the inhibitory effect would be observed since [$^3$H]sildenafil binding would be strongly inhibited by competition. The results were generally consistent with the relative affinity of cGMP for the GAF domains ($K_D$=0.2 μM) and catalytic site ($K_m$=5 μM) of PDE5, particularly considering that the sildenafil concentration in the reaction was below the optimum concentration for stimulating cGMP binding to the GAF domains. The results of FIG. 8 were reproduced using Method A for filtration (not shown), and 2–5 fold stimulations by cGMP were obtained in 6 experiments using both methods.

Figure 9:
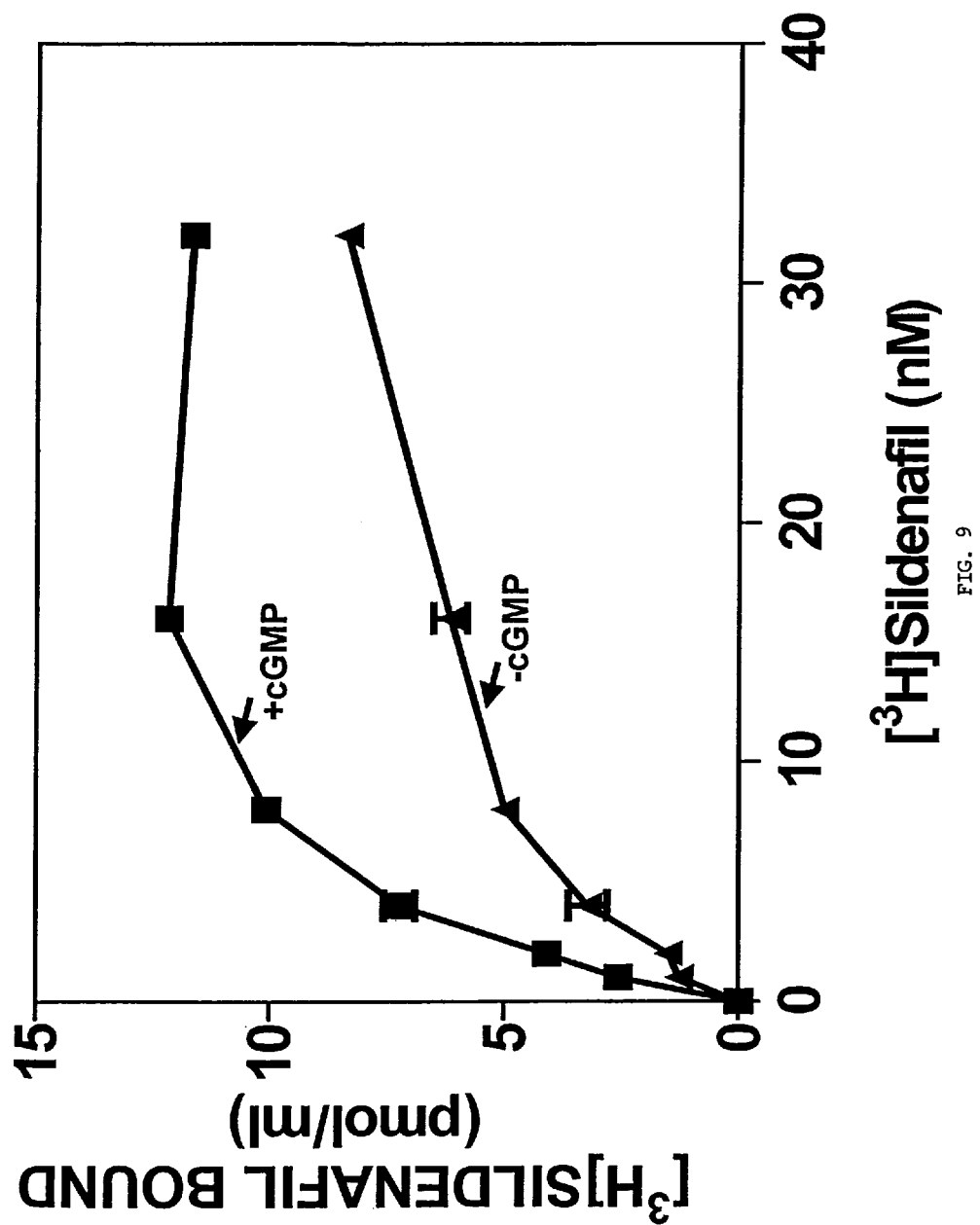
FIG. 9—Effect of [$^3$H]sildenafil concentration on cGMP stimulation of binding. Conditions were as in FIG. 8 using 1.5 pmol/ml final concentration of PDE5 (added concentration=40 pmol/ml). Units are pmol/ml added PDE5. Reactions were performed in absence and presence of 10 nmol/ml cGMP. Filtration was performed as described for Method B. Values are mean±SEM of triplicates in a single experiment. The experiment was done three times with similar results. Prism graphics (non-linear regression) were used to calculate $K_D$ and $B_{max}$ for [$^3$H]sildenafil binding.

In order to investigate the mechanism of the stimulatory effect of cGMP on [$^3$H]sildenafil binding, the optimum stimulatory concentration of cGMP (10 μM) observed in FIG. 8 was tested using various concentrations of [$^3$H] sildenafil in the Method B binding reaction (FIG. 9). It was calculated from results of three separate experiments each done in triplicate that the average [$^3$H]sildenafil binding affinity increased from $K_D$=8.3±1.8 nM in absence of cGMP to $K_D$=4.8±0.8 nM in presence of cGMP, while the Bmax increased only slightly from 10.6±0.7 pmol/ml to 15.5±1.2 pmol/ml. Using 64 nM [$^3$H]sildenafil in presence of cGMP, the stoichiometry of binding was calculated to be 0.61±0.13 mol (n=3) [$^3$H]sildenafil bound per mol PDE5 subunit.

The interpretation that binding of [$^3$H]sildenafil to the catalytic site of PDE5 is stimulated by cGMP binding to the allosteric sites of the enzyme predicts that binding of the natural ligand, cGMP, to the catalytic site would be stimulated by cGMP binding to the allosteric sites. Such studies would be difficult since cGMP interacts at both types of site simultaneously, and direct measurement of cGMP binding to the catalytic site has not been achieved to date. However, a recent report (Okada & Asakawa, 2002) asserting that cGMP binding at the allosteric sites stimulates catalytic activity is consistent with our interpretation.

Competition Assays. Potencies for sildenafil, tadalafil, and vardenafil were also determined by competition studies. FIG. 10 shows the effect of increasing concentrations of unlabeled vardenafil on binding of 3 nM [$^3$H]tadalafil. The $EC_{50}$ value was calculated from GraphPad Prism graphics using a sigmoidal dose-response curve. Since $EC_{50}$ values were determined using a [$^3$H]inhibitor concentration at the approximate $K_D$ value for PDE5, the Cheng and Prusoff/ Chou equation (Cheng & Prusoff, 1973; Chou, 1974) could be applied to calculate the $K_D$ from $EC_{50}$ by dividing $EC_{50}$ values by two (Table 2). It can be seen that ½ $EC_{50}$ was in general agreement with the $K_D$ or $IC_{50}$ for each inhibitor, and the order of potency for the inhibitors was retained. The three ½ $EC_{50}$ values for unlabeled inhibitor in competition with either [$^3$H]vardenafil, [$^3$H]sildenafil, or [$^3$H]tadalafil, were similar. This suggested that the inhibitors compete for the same site on PDE5.

TABLE 2

½ EC$_{50}$ VALUES FOR PDE5 INHIBITORS

|  | Tadalafil | Sildenafil | Vardenafil |
|---|---|---|---|
| [$^3$H]Vardenafil | 3.16 ± 1.3 | 12.8 ± 1.1 | 0.42 ± 0.1 |
| [$^3$H]Sildenafil | 2.47 ± 0.3 | 10.6 ± 1.1 | 0.25 ± 0.1 |
| [$^3$H]Tadalafil | 2.5 ± 1.5 | 11.7 ± 2.2 | 0.59 ± 0.4 |

Increasing concentrations of unlabeled inhibitor were added to 2 ml of binding reaction mixture that contained either 0.5 nM [$^3$H]vardenafil, 4 nM [$^3$H]sildenafil, or 3 nM [$^3$H]tadalafil.
Values given in nM.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

VI. REFERENCES

The following references, to the extent that they provide exemplary procedural or other details supplementary to those set forth herein, are specifically incorporated herein by reference:

U.S. Pat. No. 4,745,051
U.S. Pat. No. 4,879,236
U.S. Pat. No. 4,879,236
U.S. Pat. No. 5,077,214
U.S. Pat. No. 5,155,037
U.S. Pat. No. 5,162,222
U.S. Pat. No. 5,169,784
U.S. Pat. No. 5,278,050
U.S. Pat. No. 5,498,540
U.S. Pat. No. 5,759,809
Aravind and Ponting, *Trends Biochem. Sci.*, 22:458–459, 1997.
Ayres et al., *Virology*, 202(2):586–605, 1994.
Ballard et al., *J. Urol.*, 159:2164–2171, 1998.
Beavo et al., *J. Biol. Chem.*, 246:3841–3846, 1971.
Blissard and Rohrmann, *Virology*, 170(2):537–555, 1989.
Boolell et al., *Int. J. Impotence Res.*, 8:47–52, 1996.
Bradford, *Anal. Biochem.*, 72:248–254, 1976.
Capaldi et al., *Biochem. Biophys. Res. Comm.*, 74(2):425–433, 1977.
Carson et al., *Virology*, 182(1):279–286, 1991.
Charbonneau et al., *Proc. Natl. Acad. Sci. USA*, 87:288–292, 1990.
Charbonneau, In: *Cyclic Nucleotide Phosphodiesterases: Structure, Regulation and Drug Action*, Beavo and Houslay (eds.), 267–296, Wiley, N.Y., 1990.
Charlton and Volkman, *Virology*, 197(1):245–54, 1993.
Cheng & Prusoff, *Biochem. Pharmacol.*, 22:3099–108, 1973.
Chou, T., *Mol. Pharmacol.*, 10:235–47, 1974.
Conti, *Mol. Endocrinol.*, 14:1317–1327, 2000.
Corbin et al., *Mol Pharmacol* 63:1364–72, 2003.
Corbin and Francis, *J. Biol. Chem.* 274:13729–13732, 1999.
Corbin et al., *Eur. J. Biochem.*, 267:2760–2767, 2000.
Corbin et al., *Methods Enzymol.*, 159:74–82, 1988.
Degerman et al., *J. Biol. Chem.*, 272:6823–6826, 1997.
Fawcett et al., *Proc. Natl. Acad. Sci. USA*, 97:3702–3707, 2000.
Flockhart and Corbin, In: *Brain Receptor Methodologies*, Marangos et al., (eds.), 209–215, Academic Press, Inc., FL, 1984.
Francis and Corbin, *Methods Enzymol.*, 159:722–729, 1988.
Francis et al, In: *Cyclic Nucleotide Phosphodiesterases: Structure, Regulation, and Drug Action*, Beavo and Houslay (eds.), 117–140, John Wiley & Sons, NY, 1990.
Francis et al., *J. Biol. Chem.*, 269:22477–22480, 1994.
Francis et al., *J. Biol. Chem.*, 277:47581–47587, 2002.
Francis et al., *Prog. Nucleic Acid Res. Mol. Biol.*, 65:1–52, 2001.
Francis et al., *Int J Impot Res* 15(5):369–72, 2003.
Fujishige et al., *J. Biol. Chem.*, 274:18438–18445, 1999.
Gopal et al., *Eur. J. Biochem.*, 268:3304–3312, 2001.
Guarino and Summers, *J. Virol.*, 57(2):563–571, 1987.
Liu et al., *Biochemistry*, 40:10179–10186, 2001.
Liu et al., *Cellular Signalling*, 13:1–7, 2001.
Martignoni et al., *Int. J. Clin. Pharmacol. Ther. Toxicol.*, 20(11):543–5, 1982.
Martins et al., *J. Biol. Chem.*, 257:1973–1979, 1982.
McAllister-Lucas et al., *J. Biol. Chem.*, 268:22863–22873, 1993.
Mullershausen et al., *J. Cell Biol.*, 155:271–278, 2001.
Murthy, *Biochem. J.*, 360:199–208, 2001.
O'Reilly et al., *Hum. Genet.*, 90(3):275–278, 1992.
Okada and Asakawa, *Biochemistry*, 41:9672–9, 2002.
Remington's Pharmaceutical Sciences, 15$^{th}$ ed., pages 1035–1038 and 1570–1580, Mack Publishing Company, Easton, Pa., 1980.
Rybalkin et al., *J. Biol. Chem.*, 277:3310–3317, 2002.
Saenz de Tejada et al., *Int. J. Impot. Res.*, 13:282–90, 2001.
Schneider et al., *Eur. J. Pharmacol.*, 127:105–115, 1986.
Soderling et al., *Proc. Natl. Acad. Sci. USA*, 96:7071–7076, 1999.
Stroop and Beavo, *J. Biol. Chem.*, 266:23802–23809, 1991.
Thiem and Miller, *J. Virol*, 63(11):4489–4497, 1989.
Thomas et al., *J. Biol. Chem.*, 265:14964–14970, 1990a.
Thomas et al., *J. Biol. Chem.*, 265:14971–14978, 1990b.
Turko et al., *J. Biol. Chem.*, 271:22240–22244, 1996.
Turko et al., *Mol. Pharmacol.*, 56:124–130, 1999.
Volkman et al., *Curr. Top Microbiol. Immunol.*, 131:103–118, 1986.
Weber, *Adv. Protein Chem.*, 29:1–83, 1975.
Whitford et al., *J. Virol.*, 63(3):1393–1399, 1989.
Williams et al., *J. Gen. Virol.*, 70(Pt1): 187–202, 1989.
Workman and Kingston, *Annu. Rev. Biochem.*, 67:545–579, 1998.
Wyatt et al., *Am. J. Physiol. Heart Circ. Physiol.*, 274:H448–H455, 1998.
Yamazaki et al., *J. Biol. Chem.*, 255:11619–11624, 1980.

What is claimed is:

1. A method of assaying for binding of a test compound to a phosphodiesterase (PDE) comprising:
    (a) providing a PDE;
    (b) mixing said PDE with a positively-charged peptide or polypeptide and a test compound;
    (c) passing the mixture of step (b) through a filter;
    (d) washing said filter with an ionic detergent solution; and
    (e) measuring test compound associated with said filter, wherein test compound retained on said filter indicates binding of said test compound to said PDE, and wherein said binding of said test compound to PDE is measured at or near stoichiometric levels.

2. The method of claim 1, wherein said PDE is PDE1, PDE2, PDE3, PDE5, PDE6, PDE7, PDE8, PDE9, PDE10 or PDE11.

3. The method of claim 1, wherein said PDE is PDE2, PDE5, PDE6 or PDE11.

4. The method of claim 1, wherein said test compound is labeled, and measuring comprises assessing filter-associated label.

5. The method of claim 4, further comprising performing on said test compound a control reaction having steps (b)–(e) of claim 1 wherein a-PDE is absent from step (b).

6. The method of claim 4, further comprising performing on a control reaction having steps (a)–(e) of claim 1 with a known PDE-binding compound.

7. The method of claim 6, wherein said known PDE-binding compound is sildenafil, vardenafil or cGMP, and said PDE is PDE5.

8. The method of claim 4, wherein said label is a radioactive label, a fluorescent label, a dye, a chemilluminescent label, an enzymatic label, or a ligand.

9. The method of claim 8, wherein said label is a radioactive label.

10. The method of claim 9, wherein said radioactive label is $^3$H.

11. The method of claim 8, wherein said label is a fluorescent label.

12. The method of claim 11, wherein said fluorescent label is fluorescein, rhodamine, green fluorescent protein, and red fluorescent protein.

13. The method of claim 8, wherein said label is a chemilluminescent label.

14. The method of claim 13, wherein said chemilluminescent label is luciferase.

15. The method of claim 1, wherein step (b) is performed at less than 15° C.

16. The method of claim 15, wherein step (b) is performed at about 4° C.

17. The method of claim 1, further comprising pre-wetting said filter with an ionic detergent solution.

18. The method of claim 1, wherein said ionic detergent solutions comprises Triton X-100.

19. The method of claim 8, wherein measuring comprises scintillation counting.

20. The method of claim 1, wherein said PDE is mixed with said positively-charged peptide or polypeptide prior to mixing with said test compound.

21. The method of claim 1, wherein said PDE is derived from a tissue extract.

22. The method of claim 1, wherein said PDE is recombinant PDE.

23. The method of claim 1, wherein said PDE is purified PDE.

24. The method of claim 1, wherein said positively-charged peptide or polypeptide is a histone.

25. The method of claim 1, wherein the mixture of step (b) further comprises or is further mixed with a known PDE-binding compound that is labeled, and measuring comprises assessing filter-associated label, wherein a reduction in filter-associated label, as compared to a similar control reaction lacking said test compound, indicates binding of said test compound to said PDE.

26. The method of claim 25, wherein said known PDE-binding compound is sildenafil, vardenafil or cGMP, and said PDE is PDE5.

27. The method of claim 25, wherein said label is a radioactive label, a fluorescent label, a dye, a chemilluminescent label, an enzymatic label, or a ligand.

28. The method of claim 27, wherein said label is a radioactive label.

29. The method of claim 28, wherein said radioactive label is $^3$H.

30. The method of claim 27, wherein said label is a fluorescent label.

31. The method of claim 30, wherein said fluorescent label is fluorescein, rhodamine, green fluorescent protein, and red fluorescent protein.

32. The method of claim 27, wherein said label is a chemilluminescent label.

33. The method of claim 32, wherein said chemilluminescent label is luciferase.

34. The method of claim 25, further comprising performing a similar control reaction wherein said mixture lacks said test compound.

35. The method of claim 25, further comprising performing on said test compound and said known PDE-binding compound a control reaction having steps (b)–(e) of claim 1 wherein a PDE is absent from step (b).

36. The method of claim 1, wherein said filter is a paper filter, a nitrocellulose filter, a glass microfiber filter or a quartz microfiber filter.

37. The method of claim 36, wherein said paper filter is a Whatman 0.45μm filter.

* * * * *

UNITED STATES PATENT AND TRADEMARK OFFICE
CERTIFICATE OF CORRECTION

| | | |
|---|---|---|
| PATENT NO. | : 7,217,527 B2 | |
| APPLICATION NO. | : 10/824771 | |
| DATED | : May 15, 2007 | |
| INVENTOR(S) | : Corbin et al. | |

It is certified that error appears in the above-identified patent and that said Letters Patent is hereby corrected as shown below:

Column 27, line 15, delete "a-PDE" and insert --a PDE-- therefor.

Signed and Sealed this

Sixth Day of November, 2007

JON W. DUDAS
*Director of the United States Patent and Trademark Office*